United States Patent [19]

Wheeler

[11] Patent Number: 5,036,863
[45] Date of Patent: Aug. 6, 1991

[54] CONDOM ARTICLES, AND APPARATUS AND METHOD FOR MAKING AND USING THE SAME

[75] Inventor: Robert G. Wheeler, Greenbank, Wash.

[73] Assignee: Family Health International, Durham, N.C.

[21] Appl. No.: 568,426

[22] Filed: Aug. 16, 1990

Related U.S. Application Data

[62] Division of Ser. No. 271,884, Nov. 15, 1988, Pat. No. 4,964,416.

[51] Int. Cl.⁵ .............................................. A61F 6/04
[52] U.S. Cl. ...................................... 128/844; 128/918
[58] Field of Search ................. 128/842, 849, 79, 918; 604/330, 347–353

[56] References Cited

U.S. PATENT DOCUMENTS

| | | | |
|---|---|---|---|
| D. 253,009 | 9/1979 | Okamoto | D24/99 |
| 749,382 | 1/1904 | Henderson | 604/350 |
| 1,113,561 | 10/1914 | Jorgenson | 604/330 |
| 2,285,981 | 6/1942 | Johns | 604/349 |
| 2,410,460 | 11/1946 | Robinson | 128/294 |
| 2,433,538 | 12/1947 | Warner | 128/294 |
| 2,484,356 | 10/1949 | Ribeiro | 604/347 |
| 2,488,938 | 9/1948 | Wayne | 604/353 |
| 2,577,345 | 12/1951 | McEwen | 128/294 |
| 2,586,674 | 2/1952 | Lonne | 128/294 |
| 2,604,092 | 7/1952 | Brown | 604/352 |
| 3,037,508 | 6/1962 | Friedman | 604/330 |
| 3,295,145 | 1/1967 | Ericson | 604/330 |
| 3,361,857 | 1/1972 | Maddison | 264/0.5 |
| 3,364,932 | 1/1968 | Beach | 604/352 |
| 3,559,651 | 2/1971 | Moss | 604/349 |
| 3,759,254 | 9/1973 | Clark | 128/79 |
| 4,004,591 | 1/1977 | Freimark | 604/347 |
| 4,009,717 | 3/1977 | Allen | 128/842 |
| 4,022,213 | 5/1977 | Stein | 604/350 |
| 4,232,675 | 11/1980 | Meldahl | 604/353 |
| 4,275,812 | 6/1981 | Poncy et al. | 206/278 |
| 4,332,243 | 6/1982 | Gutnick | 128/844 |
| 4,354,494 | 10/1982 | Hogan | 128/194 |
| 4,432,357 | 2/1984 | Pomeranz | 128/79 |
| 4,446,860 | 5/1984 | Gutnick | 128/844 |
| 4,475,910 | 10/1984 | Conway et al. | 604/352 |
| 4,484,918 | 11/1984 | Omley | 604/349 |
| 4,576,156 | 3/1986 | Dyke | 128/844 |
| 4,626,250 | 12/1986 | Schneider | 604/349 |
| 4,735,621 | 4/1988 | Hessel | 604/349 |
| 4,781,709 | 11/1988 | Grubman | 604/349 |
| 4,784,655 | 11/1988 | Campion | 604/349 |
| 4,794,929 | 1/1989 | Robichaud | 128/844 |
| 4,795,425 | 1/1989 | Pugh | 128/844 |
| 4,798,600 | 1/1989 | Meadows | 604/347 |
| 4,955,392 | 9/1990 | Sorkin | 128/844 |

FOREIGN PATENT DOCUMENTS

| | | | |
|---|---|---|---|
| 0147072 | 7/1985 | European Pat. Off. | |
| 2020280 | 11/1971 | Fed. Rep. of Germany | |
| 2349361 | 4/1975 | Fed. Rep. of Germany | |
| 0663151 | 11/1987 | Switzerland | 128/844 |
| 1595711 | 8/1981 | United Kingdom | |

Primary Examiner—Robert A. Hafer
Assistant Examiner—Michael Brown
Attorney, Agent, or Firm—Steven J. Hultquist

[57] ABSTRACT

Condoms are disclosed of the type having a main sheath portion closed at a distal end and open at a proximal end thereof, which are amenable to construction from thermoplastic elastomeric materials. In one preferred aspect, such condoms have an annular-shaped sealing element, formed of an elastic material, circumscribing an interior opening of smaller size than the proximal end opening of the condom, and joined at the outer periphery of the sealing element to the main sheath, at or in the vicinity of the proximal end opening. Such construction thereby provides a membrane dam in the proximal segment of the condom to enhance its effectiveness as a contraceptive and to minimize the incidence of sexually transmitted diseases. Also disclosed are various condom manufacturing and processing apparatuses, as well as applicators for applying the condoms to the penis of a wearer.

14 Claims, 11 Drawing Sheets

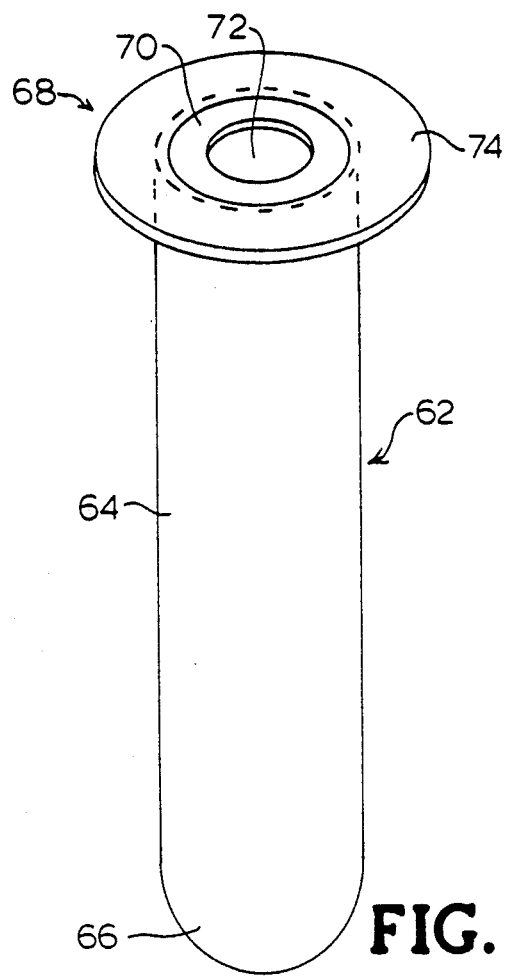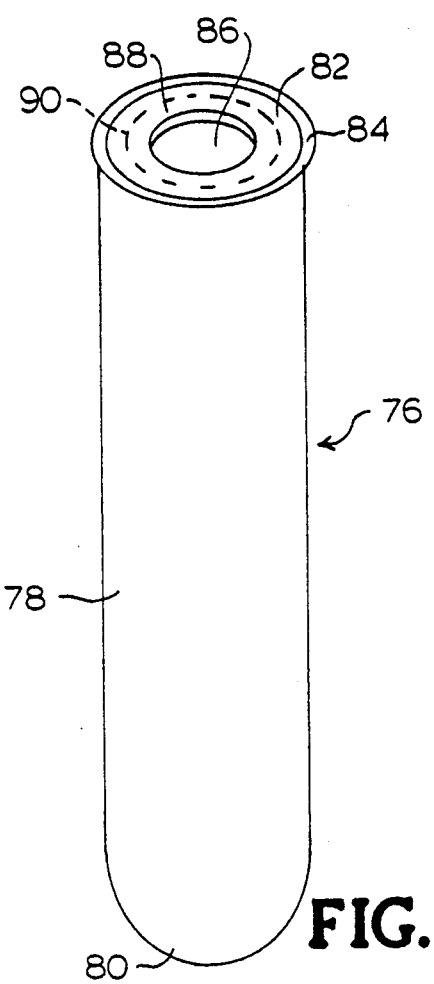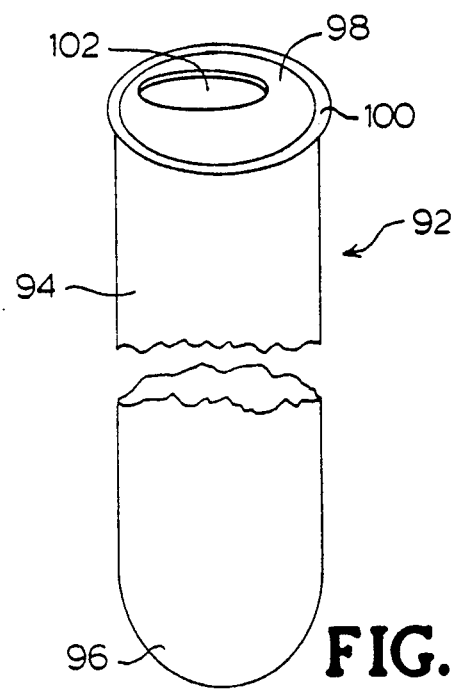

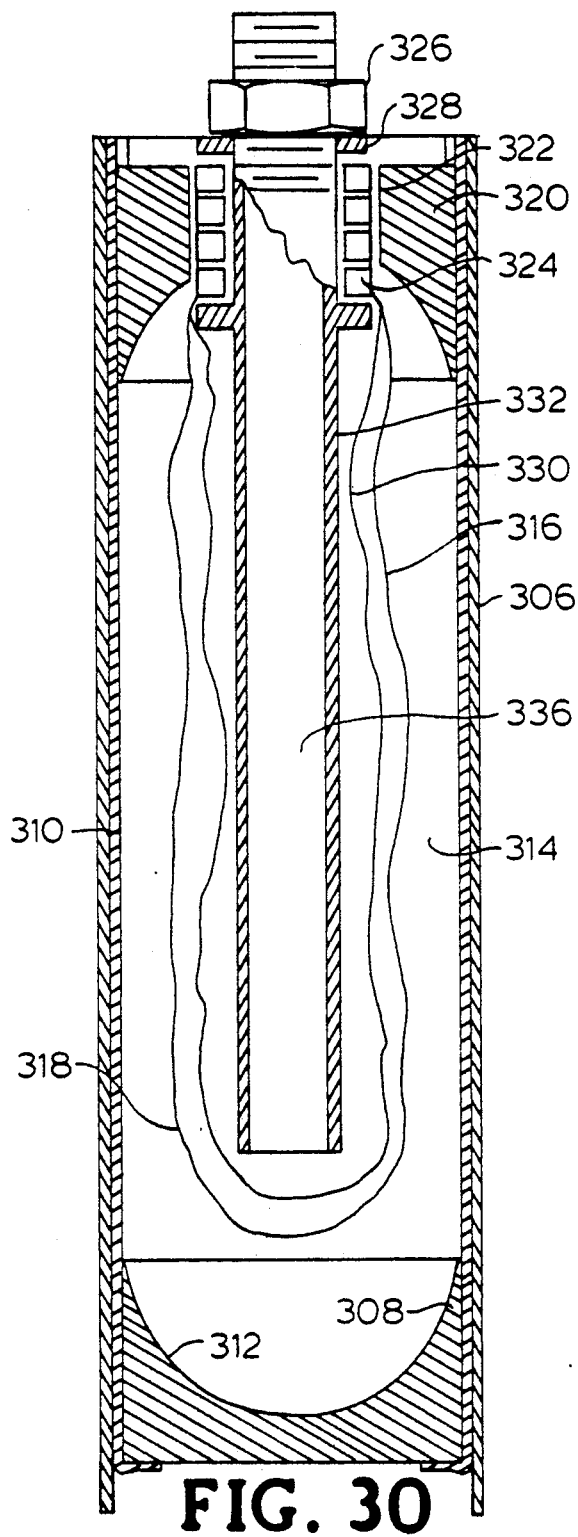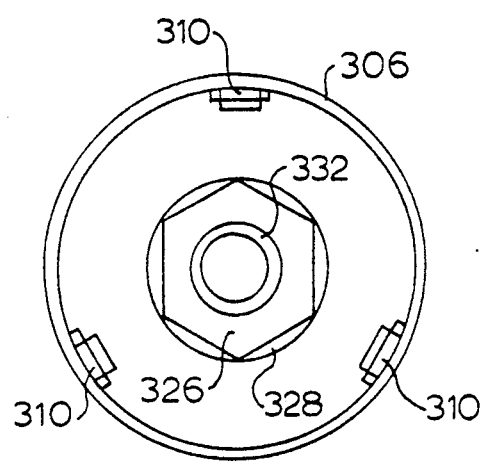
FIG. 30
FIG. 31

CONDOM ARTICLES, AND APPARATUS AND METHOD FOR MAKING AND USING THE SAME

BACKGROUND OF THE INVENTION

1. Cross Reference to Related Application

This is a division of U.S. application Ser. No. 271,884 filed Nov. 15, 1988, and issued Oct. 23, 1990 as U.S. Pat. No. 4,964,416.

2. Field of the Invention

The present invention generally relates to condom articles and to method and apparatus for making and using the same.

3. Description of the Art

In recent years, there has been a significant increase in the incidence and spread of sexually transmitted diseases, and this phenomenon has in turn caused an increased use of condoms as a prophylatic measure to reduce the risk of infection and transmission of such diseases.

Among the reasons for the increase in incidence and rate of transmission of sexually transmitted diseases (STD's) are the development of increasingly antibiotic-resistant strains of disease-causing organisms, e.g., those responsible for diseases such as syphilis and gonorrhea. Another factor has been the absence of any effective cure for acquired immunodeficiency syndrome (AIDS).

Recent disclosures by the Centers for Disease Control (Washington and Atlanta), and reports at the Third International AIDS Conference in Washington, D.C. in June, 1987, have focused international attention on the proliferation of acquired immunedeficiency syndrome (AIDS) in the general population, beyond the originally defined high-risk classification groups of homosexuals, bisexuals, intravenous drug users, and Haitain/African groups.

The diseases with which AIDS has been or is suspected to be linked include Pneumocystis carinii pneumonia, Kaposi's sarcoma, esophageal or bronchopulmonary candidiasis, extrapulmonary cryptococcosis, cytomegalovirus internal organ infection, disseminated Mycobacterium avium complex or M. kansasii infection, chronic herpes simplex ulceration, chronic cryptosporidiosis enteritis, toxoplasmosis of the brain, high-grade B-cell non-Hodgkin's lymphoma, disseminated histoplasmosis, chronic isosporiasis enteritis, and lymphoid interstitial pneumonia in children.

In a recent San Francisco cohort study reported in "AIDS: The Cost in Health and Lives," Selik, M. D. Richard M., et al, *The Internist*, April, 1987, p.p. 6 et seq., there was found to be, for every case of AIDS in the group studied, nine cases of other HIV-related morbidity. As also indicated in this article, cohort follow-up studies indicate that the proportion of HIV-infected persons who will ultimately develop AIDS ranges from 25% to 50% or more depending on the length of follow-up and the patient's clinical status at the beginning of the study. Mathematical modeling of this trend in reported AIDS cases has led to a projection that the cumulative total of AIDS cases will be 270,000 by 1991, and the number reported that year alone will be 74,000.

Against the foregoing background, and the recognition that condoms afford a safe, low cost, and generally reliable means for combating the spread of STD's, including AIDS, there has been an increased demand for condoms.

Currently, most condoms are produced from a latex resin via a dipping process in which a cylindrical and rounded-end mold is dipped into a resin bath, so that the mold is coated with a thin layer of the latex material. The thickness of the latex coating on the mold is dependent on the viscosity of the latex, and the speed of extracting the mold from the latex bath. Similar latex dipping processes have been employed with suitably shaped molds to form tight-fitting gloves such as surgical gloves.

The above-described latex resin dipping process has been utilized for decades, and yields a generally satisfactory barrier product at reasonable cost.

With the recent spread of AIDS in the general population and the resurgence of condom usage in sexual activities, there has been interest in improving the strength and reliability characteristics of condoms, and of achieving improvements in manufacturing processes and economics, to further combat the spread of STD's generally, and AIDS specifically, as well as to provide a safe and reliable contraceptive means.

U.S. Pat. No. 4,576,156 issued Mar. 18, 1986 to Manfred F. Dyke discloses a condom formed of a thermoplastic polyurethane material, having a generally cylindrical configuration with an open proximal end and a closed distal end. The disclosed condom has a thickness of from about 0.01 millimeters, or less, to about 0.25 millimeters. The thermoplastic polyurethane employed to form the condom is disclosed as having: an average Shore A hardness of from about 50 to about 90; a tensile stress, at 100% of elongation, between about 300 and 1,000 psi; and a tensile stress, at 300% elongation, between about 800 and 3,000 psi. Suitable thermoplastic polyurethane species for manufacturing the condom include those set out at column 2, line 55 to column 3, line 10 of the Dyke patent, with polyether—or polyester—based urethane elastomers said to be preferred. In the manufacture of the thermoplastic polyurethane condom disclosed in the Dyke patent, a film of the polyurethane material, e.g., in the form of a 6-inch square, is heated to a temperature high enough to soften the polymer but low enough to avoid chemical degradation, preferably in a clamping frame, and at a temperature of about 400°–500° F. The heated film then is brought into contact with a preformed mandril to cause the film to assume the shape of the mandril, preferably with application of a vacuum to the system in order to bring about uniformity in wall thickness (column 3, lines 47–50 of the patent).

European patent application 0 147 072 published July 3, 1985 in the names of Robert A. Taller, et al, discloses a process for making a polyurethane condom with a uniform thickness of from about 1.5 to about 4 mils. A heat cured polyurethane prepolymer solvent solution is employed into which a mold is dipped and withdrawn for heat curing on the mold. The polyurethane prepolymer which is employed in the dipping medium is a prepolymer which is the reaction product of a polyisocyanate with at least one long chain polyol. The polyol is amorphous at room temperature, has an average molecular weight of from about 500 to about 5,000, a hydroxy number of from 225 to about 22.4, and a NCO-/OH ratio of from about 0.95:1 to about 1.1:1.

U.S. Pat. No. 4,009,717 to C. H. Allen discloses a condom comprising inner and outer sheaths, with the inner-sheath volume providing a fluid reservoir so that the interior of the inner sheath remains dry. The outer sheath is closed at one end and open at the other. The inner sheath is open at both ends inside the outer sheath, with means between the inner and outer sheath establishing a fluid-tight seal to form a fluid reservoir therebetween.

U.S. Pat. No. 4,232,675 to E. N. Meldahl discloses a modified condom of shorter length than conventionally employed, interiorly containing a spermicidal ring and a penis-supported harness assembly.

Various condom designs have been evolved which feature a double-walled chamber at the distal end of the condom containing contraceptive or medicant material. Examples include U.S. Pat. No. 4,332,243 to M. Gutnick; U.S. Pat. No. 2,410,460 to J. P. Robinson; U.S. Pat. No. 4,446,860 to M. Gutnick; and U.S. Pat. No. 2,577,345 to F. L. McEwen.

West German Offenlegungsschrift 2020280 discloses a condom comprising two sheaths inserted in each other, the inner sheath having an opening through which semen can discharge and which is fastened in place by two rubber rings.

U.S. Pat. No. 2,433,538 to H. W. Warner discloses a sperm receptacle article comprising a receptacle member having a removable container therein. The container comprises a distal receiver opening and contains absorbent material for receiving and absorbing the sperm specimen. This patent states, at column 3, lines 3-9, that sperm passes directly from the wearer through the receiver opening into the absorbent material in the removable container. It is apparent from this description that the receptacle member is placed on the male organ and the distal end of the penis is in the vicinity of the proximal wall of the sperm container, but that the penis is not inserted through the sperm container opening.

U.S. Pat. No. 2,586,674 to F. Lonne describes a prophylactic construction (see FIG. 3 of the patent, and appertaining description at column 2, lines 26-36) wherein a double-layer condom comprises an inner pellicle having annular projections or extensions transverse to the longitudinal dimension of the prophylactic.

U.S. Design Pat. No. 253,009 to T. Okamoto shows a prophylactic device whose frontal (distal) section comprises a pair of indented surface portions forming circumferential grooves in the prophylactic, transverse to the longitudinal axis thereof.

U.S. Pat. No. 3,295,145 to R. E. Erickson describes a urine collector for infants, comprising front and rear panels peripherally sealed to one another. The panels are also sealed to one another by inclined seams, extending from the outer periphery downwardly and inwardly for part of the distance to the center line of the collector, to form a throat dividing the collector into upper and lower compartments. The back panel of the collector features an oval aperture having its major axis aligned with the longitudinal axis of the collector, to accommodate the external genitals of a small child. Surrounding the aperture is a pressure sensitive adhesive for adhering the collector to the infant's skin. The patent teaches, at column 2, lines 62-65, that the collector panels preferably are formed of a substantially transparent thermoplastic film such as polyethylene, vinyl copolymers and the like, preferably from about 0.5 to 3 mils in thickness.

U.S. Pat. No. 4,022,213 to D. Stein discloses a male drip urinal comprising a tubular sleeve provided with a thin rubber sheath adapted to be stretched over the penis for sealing purposes, with an apertured resilient sheet provided across the mouth of the urinal sleeve for sealing about the base of the penis. The purpose of this sheet, which extends radially from the mouth of the urinal, is to provide a backup seal should the inner sheath tear. The sheet is carried by an annular ring forming the mouth of the urinal sleeve. The patent states at column 2, lines 8-16 that the sheet or diaphragm is in the form of a rubber disk of approximately ⅛ inch thickness having a central hole of approximately ⅜ inch diameter for sealably engaging the base of the penis, to prevent backup of urine through the mouth of the sleeve and onto the wearer's clothing.

U.S. Pat. No. 2,448,938 to A. Wayne describes a sanitary protective appliance which may, as shown in FIGS. 5 and 6 of the patent, be configured with a shield-like body portion which is of slightly convex shape in side elevation view, with an accordian-like finger portion which is foldable back against the convex face of the body portion. The finger portion is convergingly shaped from its proximal to its distal end portions. The body portion of this device contains a generally central opening forming a passage into the finger portion and comprises an integral tab to facilitate removal of the appliance after use. The rear (proximal) face of the body portion is peripherally coated with an adhesive coating material, except for the tab. The adhesive coating is overlayed with a gauze cover which is removable to affix the appliance, for covering or protecting a body appendage. The patent discloses that the accordian finger and body portion may be round or oval in cross-section, depending on the shape of the appendage on which it is to be used. The patent states, at column 3, lines 8-15, that the appliance comprising the body portion and finger-like portion "provide a protective cover for a suitable body appendage with the finger like portion providing an additional receptacle or secondary tip capable of holding puss or other extraneous matter away from the body."

U.S. Pat. No. 4,735,621 to L. Hessel discloses a tubular protective condom-like device comprising a flexible, thin-walled tube that is closed at one end and has at an opposite open end a collar-shaped, outwardly extending portion with means for radially stretching the collar or open end. In one disclosed embodiment, the device has a first outwardly extending ring-shaped means adapted for radially extending the open end, and a second outwardly extending ring-shaped means that is adapted for radially extending the closed end. The second ring-shape means thus secures or maintains the device in the vagina in a manner similar to a diaphram. The inner diameter of the device is sufficiently large to permit movement of a penis during coital contact.

It is an object of the present invention to provide improved condom articles which are readily, simply, and inexpensively formed.

It is another object of the invention to provide apparatus and methods for making and using condoms of such types.

Other objects and advantages of the present invention will be more fully apparent from the ensuing disclosure and appended claims.

SUMMARY OF THE INVENTION

In one aspect, the present invention relates to a condom article comprising a generally tubular main sheath portion formed of a flexible elastic material, closed at a distal end thereof and open at a proximal end thereof, with an annular-shape sealing element formed of a flexible elastic material circumscribing an interior opening of smaller size than the proximal end opening, the sealing element being joined at its outer periphery to the main sheath portion at or in the vicinity of the proximal end opening.

The main sheath portion and/or sealing element may be formed of a thermoplastic elastic material, and the condom may comprise diametrally opposed heat seals extending longitudinally along the main sheath portion and converging at the distal end of the main sheath portion, with the sealing element being joined to the main sheath portion at the proximal part thereof by such heat seals. Preferably, such condom, when reposed in a flat configuration with the heat seals perimetrally aligned, has the interior opening circumscribed by the sealing element and defining a substantially semi-circular cut-out in the sealing element.

In another aspect, the present invention relates to a condom comprising a generally tubular main sheath portion formed of a thermoplastic elastic material, closed at a distal end thereof and open at a proximal end thereof, the condom having a proximal segment characterized by a reentrant fold having a central opening therein of smaller size than the proximal end opening, the reentrant fold being marginally sealed to the main sheath portion at diametrally opposed side margins of the main sheath portion.

In another aspect, the present invention relates to a condom and applicator assembly, comprising an applicator ring, and a condom comprising a generally tubular main sheath portion formed of a flexible elastic material, closed at a distal end thereof and opened at a proximal end thereof, and comprising a means for compressively retaining the main sheath portion of the penis of a wearer. The compressive retention means is provided at a position which is distally spaced from the proximal open end of the main sheath portion. The section of the main sheath portion proximal to the compressive retention means is circumferentially stretched over the applicator ring such that the compressive retention means is not stretched. In an alternative embodiment, the ring-shaped applicator has a series of circumferentially spaced-apart, longitudinally extending prong elements thereon, and the condom applicator assembly comprises the pronged ring having the proximal open end of the condom stretched onto less than all of the prongs, so that upon usage, the proximal open end can be stretched over the remaining prongs to facilitate penis insertion into the condom.

Another aspect of the present invention relates to condom articles having elastic garter elements at the proximal portions thereof. In one embodiment, the condom comprises a constituent garter at the proximal end thereof retained in position by a heat seal. Such condom article is formed in a method aspect by stretching an elastic ring radially outwardly and, while the ring is in stretched condition, lappingly folding a thermoplastic sheet over the ring, followed by peripherally heat sealing the respective lapped sheet sections to one another along the longitudinally and distal edges thereof, and finally everting the heat-sealed article.

In a related aspect, a collar of thermoplastic elastic film is stretched over a heat sealing element and inserted between adjacent sheets. The adjacent sheets are then heat sealed along the longitudinal and distal edges thereof, and the heat sealing element bonds the stretched collar to the interior of the unsealed open end, thereby forming an integral heat-sealed garter for the resulting condom article.

In a related aspect, the present invention relates to a heat-formed condom with a gartered open end, and to a method for making same, wherein a small diameter condom blank of thermoformable material is placed in a larger diameter cavity and inflated therein. The open end area of the condom is subsequently unheated, while the remainder of the condom is heated to thermally relax it to the dimensions of the cavity. The unheated open end, retaining its smaller diameter, provides a garter for the condom.

And yet another aspect, the present invention relates to a heat-sealed condom with proximal end flanges, the condom being formed with a reentrant fold at its proximal end, as previously described, with the heat seals along the longitudinal edges of the condom extending only part way to the proximal end thereof, whereby flaps of the film are provided at the condom proximal opening, to aid in applying the condom to the penis.

In another aspect, the present invention relates to a condom comprising a generally tubular main sheath portion formed of a flexible elastic material, closed at a distal end thereof and open at a proximal end thereof, with an annularly shaped sealing element formed of a flexible elastic material circumscribing an interior opening of smaller size than the proximal end opening. The sealing element extends radially outwardly to a greater diametral extent than the diameter of the main sheath portion, and the sealing element is joined to the proximal open end of the main sheath portion, to provide a peripheral annular segment of the sealing element. Such peripheral portion comprises a circumferentially extending peripheral cavity having disposed therein a rigidifying element such as a fluid, foam, or solid material, whereby the rigidified peripheral portion of the sealing element provides a manually grippable extended area, to aid in application of the condom to the penis of the wearer.

The invention in a still further aspect relates to a condom article having an annular-shaped sealing element formed of elastic material circumscribing an interior opening of smaller size than the proximal end opening of the condom, and joined at its outer periphery to the main sheath portion of the condom at or in the vicinity of the proximal end opening, wherein the interior opening is circumscribed by a weakened material portion accommodating enlargement of the opening incident to application to a correspondingly sized penis of a wearer.

In another aspect, the present invention relates to a variable length condom, comprising a generally tubular main sheath portion formed of a flexible elastic material, closed at a distal end thereof and open at a proximal end thereof, wherein an intermediate length portion of the tubular main sheath is longitudinally and reentrantly lapped, and tack welded or otherwise weakly bonded, so that the length of the condom may be increased by tensional translation of the proximal portion of the condom relative to the distal portion thereof.

In another aspect, the present invention relates to a condom comprising a generally tubular main sheath portion, closed at a distal end thereof and open at a proximal end thereof, with at least one unrolling strip extending longitudinally of the main sheath portion, attached to the main sheath portion in the vicinity of the proximal end thereof, and extending distally forwardly of the distal end of the main sheath portion.

A further aspect of the invention relates to a condom comprising a generally tubular main sheath, closed at a distal end thereof and open at a proximal end thereof, wherein a proximal outer surface region of the tubular main sheath is circumferentially adherently self-lappable. By "circumferentially adherently self-lappable" is meant that the condom subsequent to installation on a wearer's penis may be circumferentially gathered or otherwise lapped to reduce its circumferential extent on the penis, with the gathered or lapped portion being adherently secured in place. In this manner, a condom of "baggy" or otherwise loose, easily applied configuration may be employed, and subsequent to application to the body of a wearer may be circumferentially "taken up" at its proximal portion to provide an adherently secured configuration for coital activity. For example, the material of construction of the tubular main sheath of the condom may be intrinsically self-adherent in character, so that mere circumferential lapping of a gathered proximal region will cause clinging of the lapped segment of the condom to the outer surface region on which the lapped material is reposed. Alternatively, the tubular main sheath of the condom may have on an outer surface at the proximal end thereof an adhesive coating, whereby circumferential lapping of the proximal end region of the condom causes the circumferentially lapped segment thereof to be adhesively bound to the adjacent outer surface area on which the lapped segment is reposed.

The present invention in another aspect relates to a method of making a condom, comprising the steps of:

(a) providing a sheet of a thermoplastic elastic film;

(b) laterally folding the sheet along a lateral fold line to provide lapped main panel portions of the folded sheet;

(c) forming an opening in the laterally folded sheet at an intermediate part of the lateral fold line;

(d) longitudinally inserting a portion of the sheet comprising the fold line reentrantly into the folded sheet to position the fold line between the folded sheet main panel portions and at a leading edge of the inserted reentrant portion; and (e) heat sealing the folded sheet along lateral peripheral margins thereof, from the inserted reentrant portion forwardly to a distal portion of the folded sheet, to sealingly enclose an interior volume of the folded sheet, with the reentrant portion heat sealed at lateral peripheral margins thereof to the lateral peripheral margins of the main panel portions of the folded sheet.

Other aspects and features of the invention will be more fully apparent from the ensuing disclosure and appended claims.

BRIEF DESCRIPTION OF THE DRAWINGS

FIG. 9 is a perspective view of a condom according to another embodiment of the invention.

FIG. 10 is a perspective view of a condom according to a further embodiment of the invention.

FIG. 11 is a perspective view of a condom according to a still further embodiment of the invention.

FIG. 30 is a partially sectioned, partially broken away view of an apparatus for thermoforming condoms.

FIG. 31 is a top plan view of the FIG. 30 apparatus.

DETAILED DESCRIPTION OF THE INVENTION, AND PREFERRED EMBODIMENTS THEREOF

Figure 1:
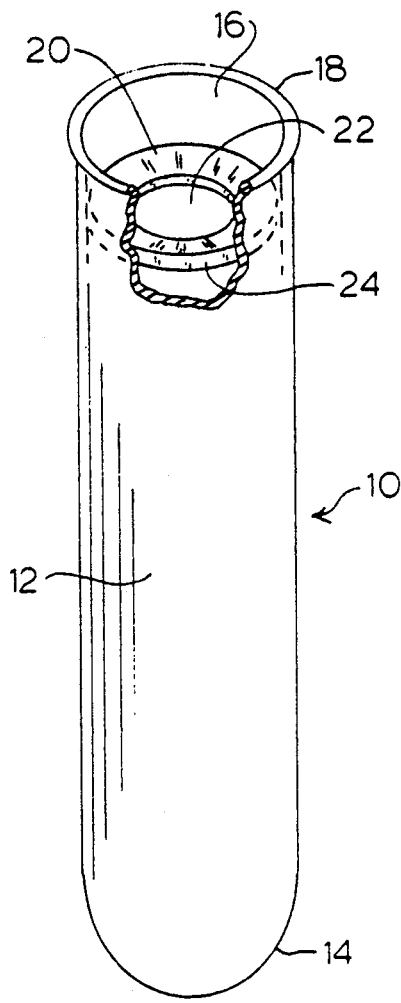
FIG. 1 is a perspective view of a condom article according to one embodiment of the present invention, featuring an annular-shaped sealing element, joined at its outer periphery to the interior walls of the main sheath portion of the condom, in the vicinity of but axially spaced from the end opening of the main sheath portion.

The condom article of the present invention is of a general type having a tubular main sheath portion, closed at a distal end and open at a proximal end thereof.

The condom of the present invention may suitably be formed by heat-sealing or otherwise joining sheets of flexible elastic material to one another to define the main sheath portion of the condom. In a preferred aspect, the condom may be formed by superposing corresponding sheets of a thermoplastic elastic material, and heat-sealing and severing same to form the condom article having a tubular main sheath portion with a closed distal end and a proximal open end. Thus, the condom so formed will have perimetral edges which are heat-sealed in the desired configuration, e.g., with a surface profile defining an elongated U-shape.

Condoms according to the present invention also may be formed by blow forming the tubular main sheath portion of the condom from a suitable thermoplastic material. As used herein, the term "blow forming" is intended to be broadly construed to include (1) blow extrusion forming, in which a tubular film of a thermoplastic material is extruded and a pressurized fluid introduced in its interior, typically an air "bubble," whose pressure and flow rate determines the dimensional characteristics of the blown tubular film, and (2) blow molding, in which a tube of heated thermoplastic material is passed into an enclosing mold where a pressurized gas inside the tubular film expands the film into contact with the interior surfaces of the mold. The diameter of the tubular main sheath portion should of course be of a size commensurate with its intended use as a barrier means overfitting a male penis.

The condom articles of the invention may be of generally cylindrical shape. Alternatively, it may be suitable in some instances to utilize the condom of the present invention in the form of a baggy-type penile enclosure which is wrapped about the penis for use, and retained in relatively looser configuration on the penis than are the condom articles of generally cylindrical shape, which closely overfit the penis, and are rolled or pulled onto the penis for use.

Thus, the specific structure of the condom article of the present invention may be widely varied, depending on the mode of application intended, and the specific materials of construction employed.

The materials useful for forming the condom articles of the invention may variously include thermoplastic elastomeric materials, as well as non-elastomeric materials such as olefinic homopolymers and copolymers, e.g., ultra-low density polyethylene.

As used herein, the term "elastomeric" in reference to thermoplastic materials useful for forming condom articles in accordance with the present invention, means a material which subsequent to elongation thereof under an applied tensional force, regains at least a significant portion of its original dimensional characteristics when the applied tensional force is released.

Illustrative of thermoplastic elastomeric materials which may find utility in the broad practice of the present invention are: polyurethane materials, as for example the polyester-based polyurethane material commercially available from Mobay Corporation (Plastics and Rubber Division, Pittsburgh, Pa.) under the trademark Texin ®, and the thermoplastic polyurethane elastomers which are commercially available from BASF Corporation (Parsippany, N.J.) under the trademark Elastollan ®; polyester elastomers, such as the block copolymers of polybutylene terephthalate and long-chain polyether glycols, which are available commercially from E. I. Du Pont de Nemours and Company, Inc. (Polymer Products Department, Engineering Polymers Division, Wilmington, Del.) under the trademark HYTREL ®; polyether blockamides, such as those commercially available from Atochem, Inc. (Glennrock, N.J.) under the trademark Pebax ®; multiblock rubber-based copolymers, particularly those in which the rubber block component is based on butadiene, isoprene, or ethylene/butylene, such as the multiblock rubber-based copolymers commercially available from Shell Chemical Company (Houston, Tex.) under the trademark Kraton ®; ethylene-octene copolymers such as those commercially available from The Dow Chemical Company (Midland, Mich.) under the trademark ATTANE ™; as well as any other suitable homopolymers and copolymers, and mixtures, alloys, and composites thereof.

Among the foregoing materials, polyether- and polyester-based polyurethanes, and multiblock rubber-based copolymers are most particularly preferred. The most preferred thermoplastic materials for forming condom articles in accordance with the present invention are the aforementioned thermoplastic polyurethane elastomers commercially available under the trademark Elastollan ®.

The composition of multiblock rubber-based copolymers employed as materials of construction for the condom articles of the present invention may be varied widely, it being understood that the non-rubber repeating units of the copolymer may be derived from any suitable monomer(s), as for example, (meth)acrylate esters, such as methyl methacrylate, cyclohexylmethacrylate, etc.; vinyl arylenes, such as styrene; etc.

In general, the non-rubber blocks in the multiblock rubber-based copolymer preferably are derived from monomer(s) which are non-elastomeric in character, so that "soft" rubber blocks and "hard" non-elastomeric blocks are provided in the multiblock copolymer. Such hard blocks may suitably be derived from monomers having a glass transition temperature ($T_g$) of at least about 50° C., with styrene being generally preferred. The rubber block of such multiblock copolymers may be formed of repeating units derived from synthetic rubbers such as butadiene, isoprene, ethylene/butylene, etc., with butadiene and ethylene/butylene elastomeric blocks generally being preferred.

The most preferred multiblock rubber-based copolymers are those having an A-B-A structure comprising polystyrene endblocks and an elastomeric midblock.

Illustrative multiblock butadiene-based copolymers which may be usefully employed in the broad practice of the present invention include those variously described in U.S. Pat. Nos. 3,297,793; 3,595,942; 3,402,159; 3,842,029; and 3,694,523, the disclosures of which hereby are incorporated by reference herein. Various multiblock butadiene-styrene copolymers may be usefully employed to form the condom of the present invention, such as the aforementioned triblock ethylene-butadiene-styrene copolymers commercially available under the trademark Kraton ™ from Shell Chemical Company (Houston, Tex.) and small block butadiene-styrene copolymers commercialized by Firestone Synthetic Rubber & Latex Company (Akron, Ohio) under the trademark Stereon ®.

In the general use of a multiblock rubber-based copolymer as the material of construction for the condom article of the present invention, the copolymer material preferably is characterized by the following physical properties: a Shore A hardness of from about 25 to about 100; a tensile strength of from about 500 to about 4500; a 300% modulus of from about 120 to about 1,000 psi; and an ultimate elongation of from about 200 to about 1400%.

With reference to the use of polyurethanes as materials of construction for the condom of the present invention, preferred material characteristics include: a specific gravity of from about 1.00 to about 1.25, a Shore A hardness from about 80 to about 100, a break tensile stress from about 4500 to about 6,000 psi; a tensile stress at 50% elongation of from about 400 to about 2400 psi, an ultimate elongation of from about 350% to about 600%, a flexural modulus of from about 4,000 to about 37,000 psi, and a tear strength of from about 500 to about 1,000 pli.

It will be recognized that processing conditions and apparatus may be varied widely in blow forming the tubular main sheath portions of condoms in accordance with the present invention, depending on the specific thermoplastic material employed in the blow forming operation, the volumetric space requirements of the process system, the method and apparatus employed for closure of the distal end of the tubular main sheath portion to form the finished condom structure, etc. The choice of specific processing conditions, materials, and the like may readily be determined for a given product application without undue experimentation, by those skilled in the art.

In blow extrusion forming of the main sheath portion of the condom, by way of example, the temperatures over a three-zone extruder may illustratively range from about 300° to about 380° Fahrenheit for a polyester-based polyurethane material or a multiblock butadiene-based styrene copolymer, while the temperature range in the same extruder for an ultra low density ethylene-octene copolymer or a polyether block amide may range from about 400° to about 450° F.; associated therewith are blow pressures which may range from 1 to 12 ounces per square inch of blown film, depending on the specific material employed.

When blow extrusion is utilized as the method for blow forming the tubular main sheath portion of the condom, the resulting tubular article has two open ends, and one of such open ends is sealingly closed to form the final condom article. The end closure operation may be carried out in any suitable manner, as for example by heat sealing, and preferably is automated so as to accommodate high speed manufacture of the condom article in high volume. Thus, the tubular body formed by blow extrusion may concurrently be sealed and severed at regular intervals along its length, to accommodate continuous processing.

The closure of the blow extruded tubular main sheath portion preferably is carried out by heat sealing, as is advantageous from the standpoint of thermoplastic materials being employed to form the condom.

The specific method of closure will depend largely on the specific material of construction employed for the tubular sheath portion of the condom, as well as its thickness. The wall thickness of the condom article may vary widely, but preferably is on the order of from about 0.05 to about 0.25 millimeter.

With such low thicknesses, it is important that the sealing method not produce differential stresses or other material deficiencies in the tubular main sheath in the vicinity of the distal end seal. Accordingly, when heat sealing is employed as a closure technique for forming the enclosed distal end of the condom, thermal impulse heat sealing is highly preferred, since it can initiate the sealing process at low temperature, with the material to be sealed thereafter quickly rising to the desired high sealing temperature, and then quickly returning to ambient temperature. Thus, rapid sealing of a localized region is effected, in a manner which prevents nearby regions of the film being sealed from experiencing substantial temperature changes, such as might otherwise result in undesirable change of material properties in the vicinity of the seal. This consideration is particularly important in thinner films, e.g., with material thicknesses on the order of 0.05 millimeter, or lower, up to approximately 0.1 millimeter.

Thus, in a continuous process blow extrusion system, wherein the blown film tube is continuously formed into discrete condom articles, the sealing method may be combined with, or otherwise effect, severing of the film into discrete tubular segments for the desired product articles. For example, it may be possible to utilize an ultrasonic sealing assembly comprising an ultrasonic horn having associated therewith a blade element as an integral part of the horn structure, which in combination with a mating anvil effects concurrent or substantially contemporaneous severing of the tubular film into discrete sequential tubular segments and ultrasonic bonding of distal ends thereof to form condom articles.

Alternatively, it may be desirable to sever the tubular blow extruded film to form discrete open-ended tubular main sheath portions, followed by a separate distal end sealing operation.

It may also be desirable in the broad practice of the present invention, as indicated, to form the condom article from flat film stock or sheet material, which is folded and heat sealed, or otherwise formed into the condom article, or the main sheath portion thereof.

As discussed hereinabove, the condom articles of the present invention may be formed in various configurations, including tubular cylindrical-type configurations, as well as "baggy"-type configurations, the choice of a specific configuration depending on the particular materials of construction and the intended packaging, storage, and use environments of the condom.

Referring now to FIG. 1, there is shown a most preferred type of condom according to the present invention. As illustrated, condom 10 comprises a main sheath portion 12 having a closed distal end 14 and an open proximal end 16. The open proximal end of the condom may be circumscribingly bounded by a ring or bead 18 of elastic material, to aid in retaining the condom on the penis of a wearer.

Figure 2:
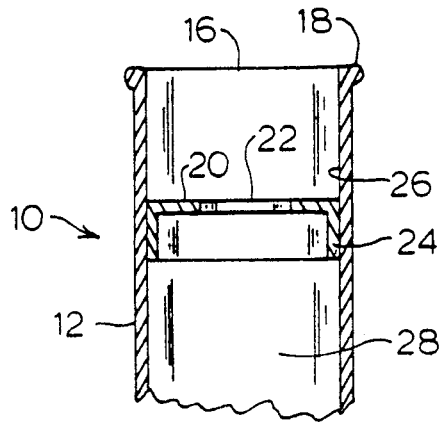
FIG. 2 is a sectional elevation view of the proximal portion of the FIG. 1 condom.

Axially spaced forwardly (distally) from the open proximal end 16 of the condom is an annular-shaped sealing element 20 circumscribing an interior opening 22 of smaller size than the proximal end opening 16. The annular sealing element is joined at its outer periphery to the inner wall of the main sheath portion by means of the downwardly depending skirt portion 24 of the sealing element, as best shown in FIG. 2, which is a cross-sectional, elevation view of the proximal part of the condom of FIG. 1. The skirt portion 24 of the sealing element may be joined to the inner wall 26 of the condom in any suitable manner, as for example by adhesive bonding, heat sealing, tack welding, ultrasonic bonding, etc.

Thus, when the condom shown in FIGS. 1 and 2 is applied to the person of a wearer, the penis is inserted through the open proximal end 16 and through the interior 22 of the annular sealing element 20, whereby the annular sealing element, at its inner radial boundary surrounding the central opening, bears compressively against the circumference of the associated portion of the penis, thereby providing an additional barrier to the leakage of semen from the condom subsequent to ejaculation.

To the extent that the elastic ring 18 bears compressively against the circumference of the base of the penis, a further enhanced protection is provided against leakage of seminal fluid from the condom, or of penetration of vaginal exudates and secretions into the interior volume 28 of the condom.

Figure 3:
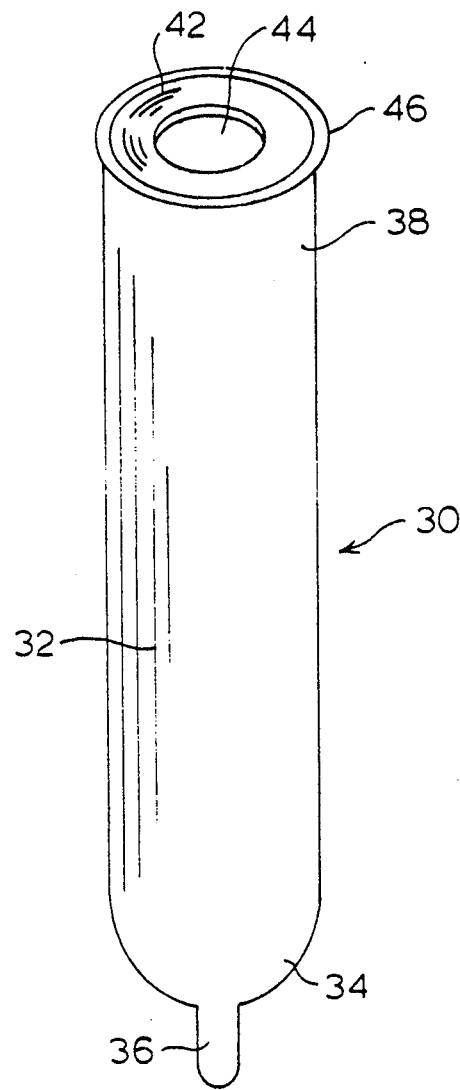
FIG. 3 is a perspective view of a condom article according to another embodiment of the invention, featuring an annular sealing element at the proximal opening of the main sheath portion of the condom.
Figure 4:
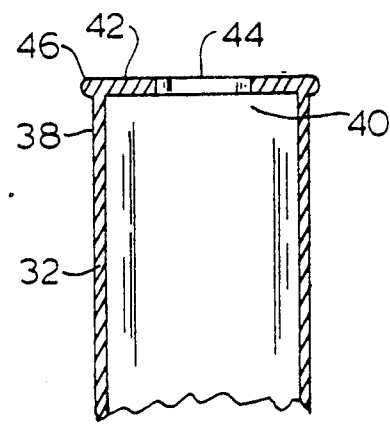
FIG. 4 is a sectional elevation view of the proximal portion of the FIG. 3 condom.

FIG. 3 is a perspective view of a condom according to another embodiment of the invention, with a corresponding cross-sectional elevation view of the proximal section thereof being shown in FIG. 4.

This condom 30 has a generally tubular main sheath portion 32 which is closed at its distal end 34, where it is provided with a distal tip reservoir 36 for retention of ejaculate.

The main sheath portion 32 has an opening 40 at its proximal end 38. Joined to the main sheath portion at this proximal end opening is an annular-shaped sealing element 42 formed of a flexible elastic material and circumscribing an interior opening 44 of smaller size than the proximal end opening 40 of the main sheath portion. The annular sealing element 42 is joined to the proximal end 38 of the main sheath portion 32 by means of weld 46. In lieu of this weld, the annular sealing element may be joined to the proximal open end of the main sheath portion of the condom in any suitable manner, as previously described with respect to the securement of the annular sealing element to the interior of the main sheath in the embodiment of FIGS. 1 and 2.

The annular sealing element in the condom constructions previously described thus functions as a dam or diaphragm which aids in preventing the exchange of body fluids between sexual partners during coital activity.

Figure 5:
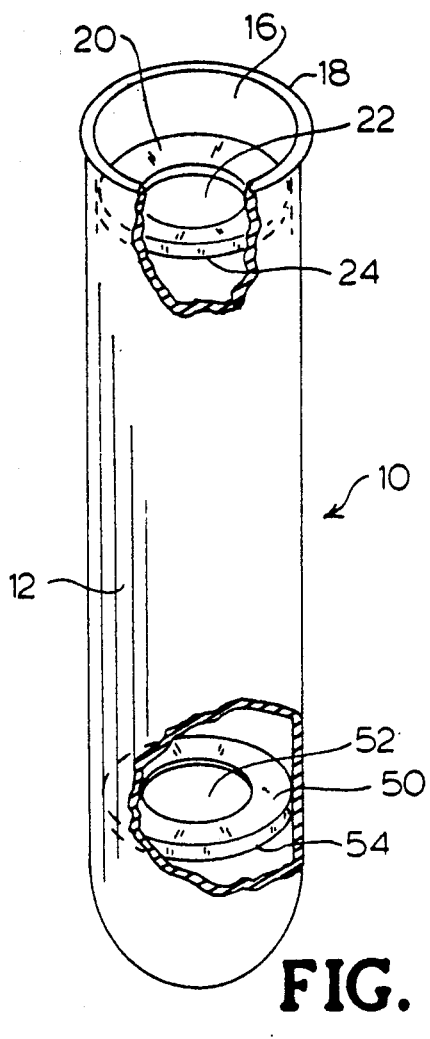
FIG. 5 is a perspective view of a condom similar to that shown in FIG. 1, but with the further addition of an annular sealing element in the distal portion of the condom.

FIG. 5 is a partially broken-away, perspective view of a condom according to another embodiment of the invention, similar to that shown in FIG. 1 (and correspondingly numbered with respect thereto), but further modified by the addition of a second annular sealing element 50, which is constructed similarly to annular sealing element 20, and is positioned forwardly thereof in the distal portion of the condom.

Thus, the annular sealing element 50 circumscribes an interior opening 52 and is attached to the inner wall 26 of the condom along the outer circumferentially extending skirt 54 of the sealing element.

Figure 7:
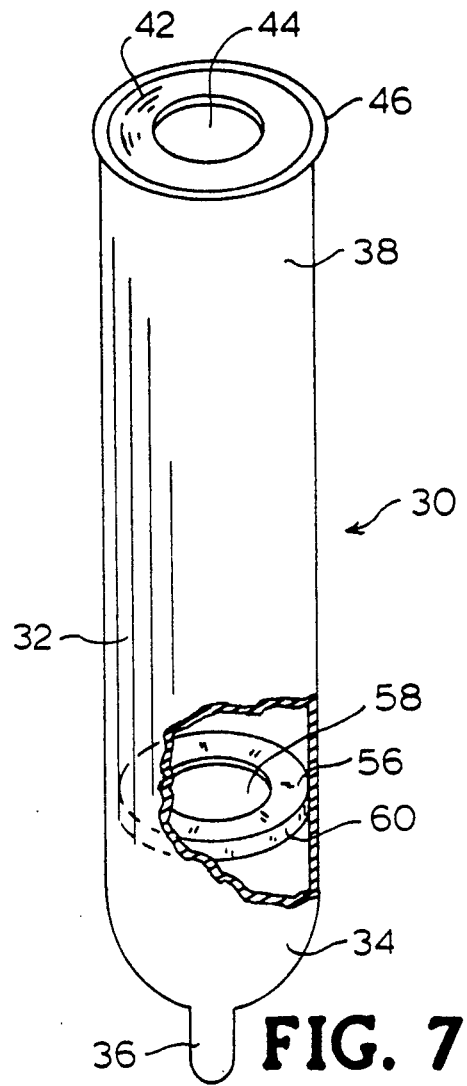
FIG. 7 is a perspective view of a condom according to another embodiment of the present invention, similar to that shown in FIG. 3, but with the provision of an additional annular sealing element in the distal portion of the condom.
Figure 6:
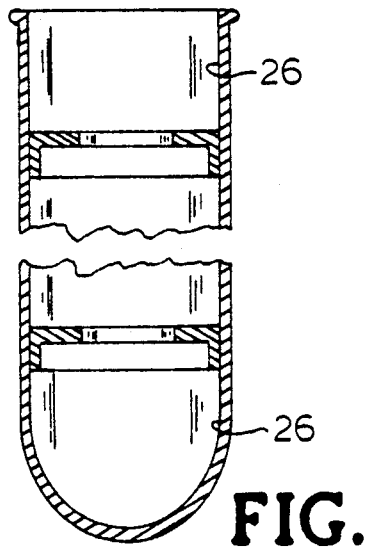
FIG. 6 is a sectional elevation view of the FIG. 5 condom.
Figure 8:
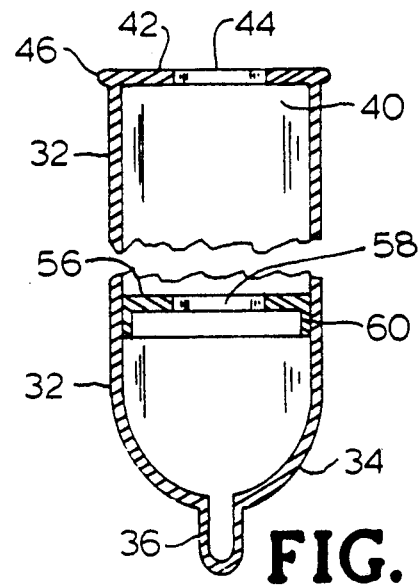
FIG. 8 is a sectional elevation view of the FIG. 7 condom.

FIG. 7 shows a partially broken-away perspective view, and FIG. 8 a sectional elevation view, of a condom of the type shown in FIGS. 3 and 4 (FIGS. 7 and 8 being numbered correspondingly with respect thereto), but modified in the provision of a distal annular sealing element 56. This distal sealing element circumscribes an interior opening 58 and is secured to the inner surface of the distal wall of the main sheath portion of the condom, by means of downwardly depending skirt 60, the skirt being joined at its upper end to the periphery of the main disk portion of the annular sealing element.

The addition of the distal annular sealing elements in the FIGS. 5–8 embodiments provides additional protection against leakage of seminal fluid out of the condom.

FIG. 9 shows a perspective view of a condom 62 comprising a tubular main sheath portion 64 having a closed distal end 66 and an open proximal end. At the proximal end of the main sheath portion is joined a donning/retention assembly 68, comprising an annular dam 70 circumscribing a central opening 72, and a radially outwardly and circumferentially extending enclosure 74, which is joined to the main disk portion of the assembly forming dam 70. The enclosure 74 may form a circumferentially continuous interior volume, which may be filled with a suitable foam, fluid, or solid material imparting sufficient rigidity to the enclosure to render it manually grippable, for manual installation of the condom on a penis of a wearer, or manual removal of the condom from the wearer's penis, subsequent to coital activity.

Alternatively, the peripheral segment 74 of the assembly 68 may be formed as a solid member, thereby providing a circumscribing flap for manual application and removal of the condom.

FIG. 10 is a perspective view of a condom 76 according to another embodiment of the invention. This condom comprises a generally tubular main sheath portion 78 having a closed distal end. The main sheath portion is open at its proximal end, and has an annular sealing element 82 joined to the upper edges of the sheath's proximal wall by means of weld or bead 84. Element 84 alternatively may constitute a resilient ring which is heat sealed to the annular sealing element 82 and the upper edges of the proximal wall of the sheath.

The annular sealing element 82 circumscribes an interior opening 86. Circumferentially surrounding the interior opening 86 is a weakened interior annular segment 88 which is circumferentially bounded by the outer extremity demarcated by dashed line 90. The weakened area 88 may for example comprise a region of reduced thickness relative to the outer circumscribing segment of the sealing element, or it may have been selectively irradiated to preferentially weaken such segment relative to the unirradiated outer segment of the sealing element, or the inner annular segment may be preferentially weakened in any other suitable manner or by any other suitable means.

The condom shown in FIG. 10 thus provides a variably sizable opening, depending on the size characteristics of the penis inserted into the condom through the central opening 86. The provision of the inner annular weakened area in the dam 82 thus may be of advantage where it is desired to accommodate a wide range of wearer penis sizes.

FIG. 11 is a perspective view of a condom 92 comprising a generally tubular main sheath portion 94 having a closed distal end 90, with a annular-shaped sealing element 98 being perimetrally joined to the open proximal end of the condom by means of circumferential weld 100. The dam element 98 has an opening 102 which is positioned off-center, as compared with the previously described annular sealing elements. Further, the opening 102 is non-circular in character. These features are intended to enhance the retainability characteristics of the condom on the penis of a wearer.

Figure 12:
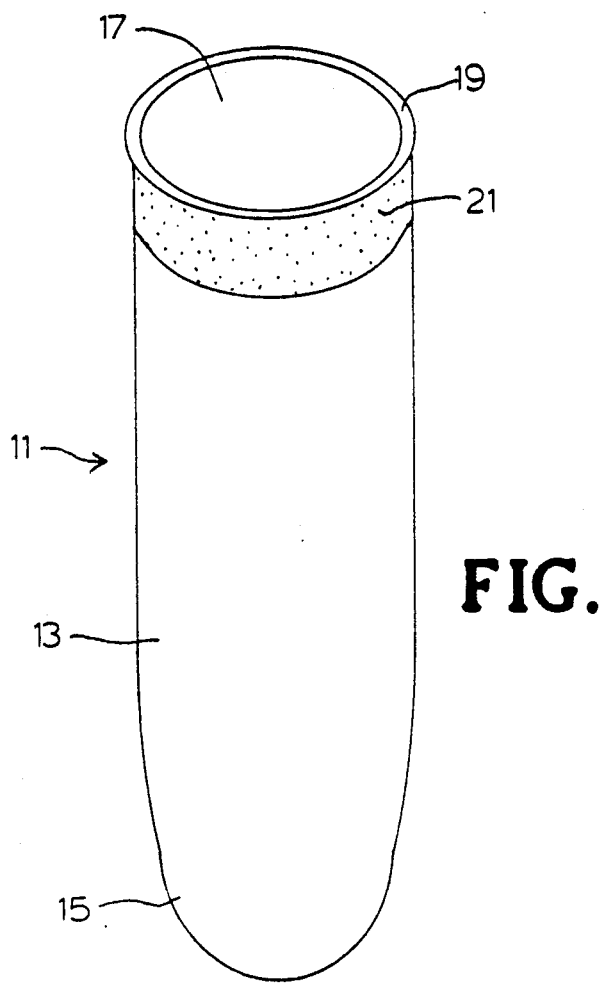
FIG. 12 is a perspective view of a condom according to another embodiment of the present invention.

FIG. 12 shows a condom 11 according to another embodiment of the present invention, featuring a main tubular sheath 13 having a closed distal end 15 and an open proximal end 17 circumscribed by rim 19. In this type of condom construction, the rim 19 preferably does not form any retentive function in application of the condom to the penis of a wearer.

Anterior to the open end 17 is a proximal length of the tubular main sheath which is provided with an outer coating 21 of a suitable adhesive material, which is tacky or otherwise self-adherent in character. The entire condom thus may be formed of a "baggy" or oversized configuration, to accommodate a varying size of penises and application to the body of a specific wearer, by installation of the condom on the wearer's penis, followed by circumferential lapping of a proximal portion of the condom as shown in FIG. 12A.

Figure 12A:
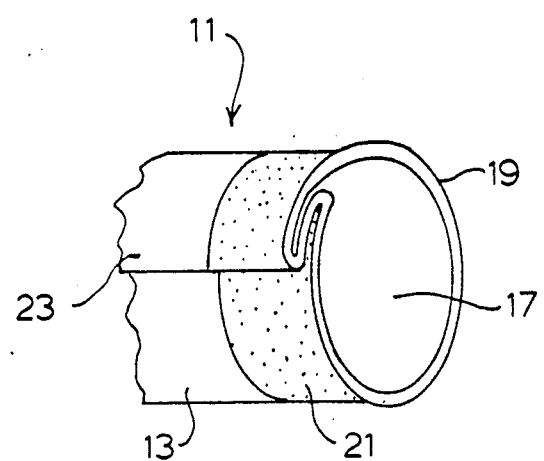
FIG. 12A is a perspective view of a proximal end section of the FIG. 12 condom, in a circumferentially lapped adherent configuration.

Referring to FIG. 12A, which shows a perspective view of a proximal portion of the FIG. 12 condom, wherein the various elements are numbered correspondingly to FIG. 12, a fold 23 of the condom may be formed at its proximal end and circumferentially lapped as shown, so that the adhesive coating 21 which is provided on the exterior surface of the tubular main sheath 13 adherently secures the fold 23 in position as shown, whereby the proximal opening 17 bounded by rim 19 is decreased in cross-sectional area, relative to the unlapped configuration shown in FIG. 12.

It will be readily apparent that in lieu of the adhesive coating 21 employed at the proximal end of the condom shown in FIGS. 12 and 12A, it may be advantageous in some instances to utilize other means for adhering a circumferential fold to the adjacent outer surface regions of the condom. Thus, any suitable adhesive strips, tapes, and the like could be used. In some instances, the material of construction of the condom itself may have sufficient "cling" or self-adhering qualities to render the need for separate adhering means superfluous; condoms formed of such materials may simply be installed on the penis of a wearer, and then circumferentially gathered or lapped to secure the same reduction in cross-sectional area and good fit on the penis of a wearer, such as is achieved by the provision of an adhesive coating in the embodiment illustratively shown in FIGS. 12 and 12A.

Figure 13:
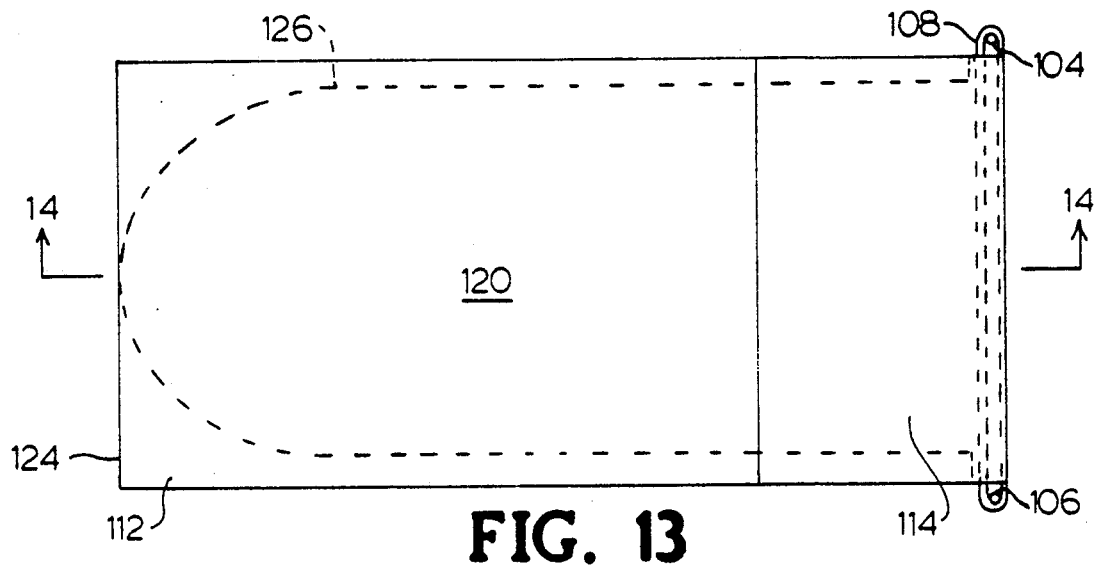
FIG. 13 is a top plan view of a folded sheet and stretched garter assembly, for forming a condom according to one embodiment of the present invention.
Figure 14:
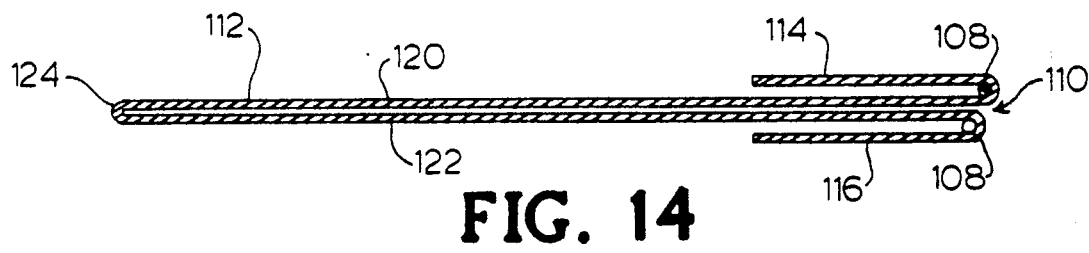
FIG. 14 is a side elevation view of a section of the FIG. 13 folded sheet/stretched garter assembly, taken along line 14—14 thereof.

FIG. 13 is a top plan view of a folded sheet/stretched elastic ring assembly, with FIG. 14 being a side elevation view of the same assembly as shown in FIG. 13, taken along section 14—14 thereof.

Figure 15:
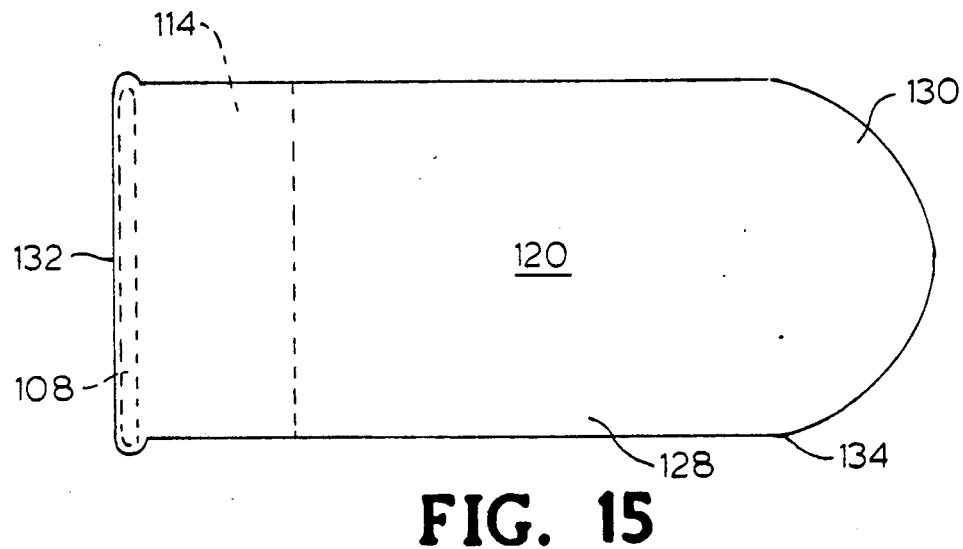
FIG. 15 is a plan view of a condom according to the present invention, formed from the folded sheet/stretched garter assembly of FIG. 13.

FIG. 15 is a top plan view of a condom article formed from the folded sheet and stretched elastic ring assembly of FIGS. 13 and 14.

With reference to FIGS. 13 and 14, a pair of transversely spaced-apart pins 104 and 106 are fixedly positioned relative to one another. For such purpose, the pins may be secured to a suitable base structure (not shown), the base being of planar horizontal character and having the pins secured to and vertically upwardly extending from the base structure. An elastic ring 108 then is stretched over the pins 104 and 106, the ring thereby circumscribing an opening 110 (see FIG. 14). Through this opening a sheet of a flexible thermoplastic material 112 is inserted and the end flaps 114 and 116 are folded back as shown in FIG. 14.

In this fashion, there is formed a folded sheet assembly comprising a proximal mouth 110 and longitudinally extending lappingly co-extensive sheet portions (layers 120 and 122 as shown in FIG. 14), the lappingly co-extensive sheet portions forming main sheet panels terminating at a distal fold line 124. The proximal extremities 114 and 116 of the folded sheet are distally extended to lap one another exteriorly of the main panels 120 and 122 of the folded sheet.

The thus-folded sheet assembly then is heat-sealed and severed along the dashed line 126 shown in FIG. 13, to provide a main sheath portion of the condom having a curved profile at its distal end, and being perimetrally heat-sealed.

After heat sealing and severing of the folded sheet assembly along line 126, the elastic ring 108 is removed from the pins retaining same, and the resulting article is everted (turned inside out), to yield the condom article shown in FIG. 15, comprising a main sheath portion 128 having a closed distal end 130 and a proximal open end 132. The condom thus features an interiorly secured elastic retaining ring 108, and is continuously heat-sealed along its perimetral edge 134 extending from the proximal opening around the entire edge surface of the condom to the corresponding opposite portion of the proximal opening, when the condom is reposed on a flat surface as shown in the plan view of FIG. 15.

It will be appreciated that the method of making a condom which is illustratively described above with reference to FIGS. 13–15, may be practiced with an elastic drawstring being employed in place of the elastic ring. Thus, an overhand knot may be tied in the elastic drawstring to form a loop therein, and the loop may be placed over the pins 106 and 108 in such a way that one drawstring extends laterally outwardly from one pin, while the other drawstring extends laterally outwardly from the other pin.

In this manner, a condom may be formed such that the ends of the drawstrings protrude from the proximal open end of the resulting condom, permitting it to be selectively tightened and tied in place on the penis of a wearer. Further, if the drawstring is constructed of a material such as a thermoplastic elastomer ribbon, a single overhand knot in the ribbon may allow the loop to be tightened and hold its tension without slipping.

Figure 16:
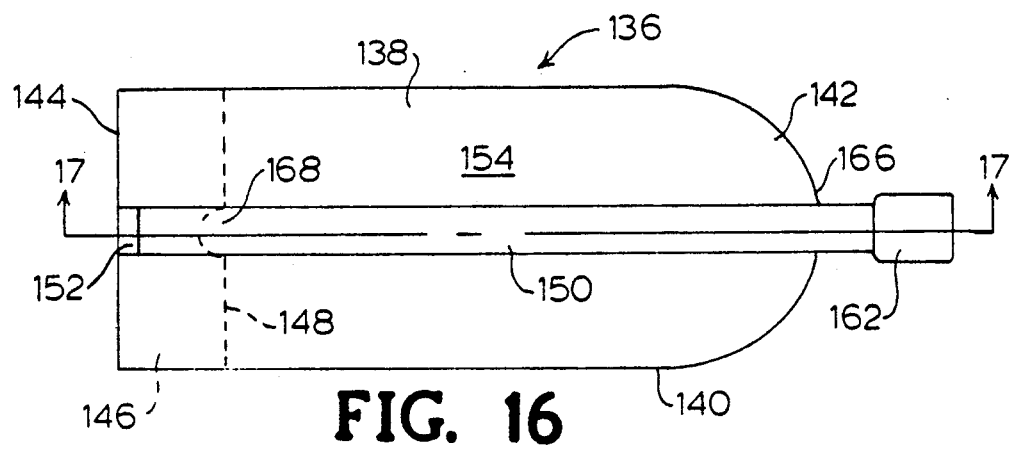
FIG. 16 is a top plan view of a condom according to a further embodiment of the invention.
Figure 17:
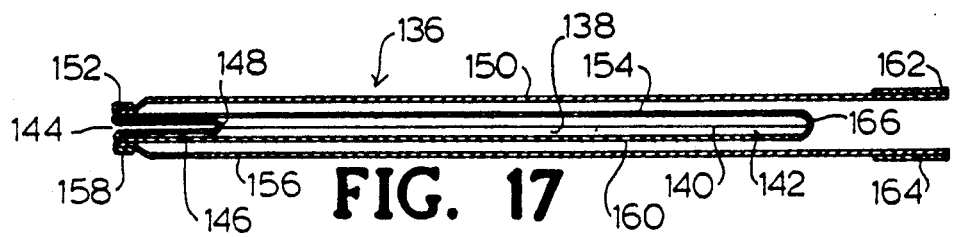
FIG. 17 is a side elevation view of a section of the FIG. 16 condom, taken along line 17—17 thereof.

FIG. 16 shows a top plan view of a condom according to the another embodiment of the invention, and FIG. 17 is a side elevation thereof along section 17—17.

The condom 136 shown in these drawings comprises a main sheath portion 138 formed by top and bottom panels 154 and 160 which are heat-sealed to one another along a perimetral edge 140 thereof, from a distal extremity 166 rearwardly to proximal opening 144, such edge seal defining an elongated U-shape, as shown in the top plan view of FIG. 16.

The condom shown in these drawings may be formed of any suitable material of construction, preferably a thermoplastic elastomer, such as a polyurethane elastomer material. The main sheath portion thus is closed at its distal end and open at its proximal end. The condom has a proximal segment characterized by a reentrant fold 146 having a central opening 168 therein of smaller size than the proximal end opening 144. The reentrant fold is sealed at its margins to the main sheath portion at diametrally opposed side margins of the main sheath portion. The reentrant fold thus has a distal leading edge 148, and forms a dam or diaghragm structure of a character similar to condom embodiments previously described herein.

Joined to the main sheath portion of the condom at the proximal extremity thereof are respective diametrally opposed unrolling strips 150 and 156, joined at their distal extremities to the respective top and bottom panels 154 and 160 of the main sheath portion, by respective seals 152 and 158.

The seals 152 and 158 may be heat seals, or may be formed by ultrasonic welding, adhesive bonding, or any other suitable methods of affixment. The unrolling strips thus extend longitudinally distally of the distal end 142 of the condom, terminating in respective grips 162 and 164, to aid in manual gripping of the unrolling strips, when the condom is supplied in a rolled configuration formed by being rolled forwardly from its proximal end to its distal end, with the manually grips 162 164 protruding from the thus-rolled condom.

By the provision of such unrolling strips, the condom may be applied to the penis of a wearer by the simple expedient of manually gripping the respective gripping portions 162 and 164 and positioning the rolled condom at the distal end of the penis, followed by rearwardly manually pulling on the unrolling strips to reverse roll the condom onto the penis, from the distal end to the base thereof.

It will be appreciated that the unrolling strips are an optional feature of the condom shown in FIGS. 16 and 17, and that the same may be omitted, with the resulting condom being susceptible of application in a conventional manner, from a rolled configuration, or otherwise by pulling the condom onto the penis of the wearer.

Figure 18:
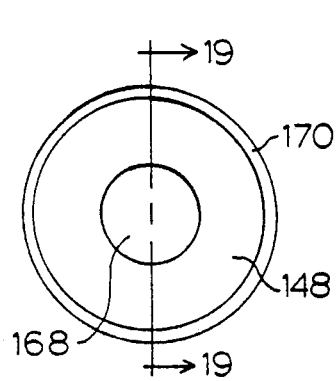
FIG. 18 is a front elevation view of a rolled condom according to another embodiment of the invention.
Figure 19:
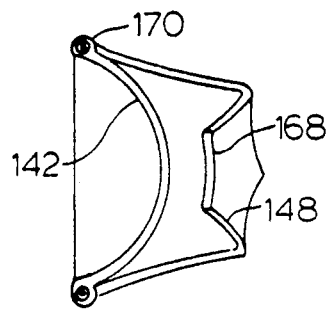
FIG. 19 is a side elevation view of a section of the FIG. 18 rolled condom, taken along line 19—19 thereof.

FIG. 18 shows a front elevation view of a rolled condom of the type shown in FIGS. 16 and 17, but without the provision of the aforementioned unrolling strips 150 and 156. FIG. 19 is a side elevation view of the rolled condom of FIG. 18, taken along line 19—19 thereof.

As illustrated, the rolled condom features a peripheral roll 170, which comprises the major length of the main sheath portion of the condom, the main sheath portion being rolled back on itself until the closed distal end 142 and the membrane dam 148 are in juxtaposition with one another. This configuration avoids retention of a rolled condom structure in packaging or storage for prolonged periods under a deleterious condition of strain on the membrane dam.

By way of example, if the central opening 168 in the membrane dam 148 has a relaxed (unstretched) diameter of 0.5 inch and the flat width of the condom is 3 inches, rolling the entire condom will stretch the ½ inch diameter opening to a diameter of about 2 inches. If the condom then is stored in this rolled condition for a prolonged period, the condom material of construction, such as a thermoplastic elastomer, will relax until the opening may be too large for some users of the condom article. In the rolled configuration shown in FIGS. 18 and 19, the membrane dam 148 is not rolled and will be in a relaxed mode until the condom is donned.

Figure 20:
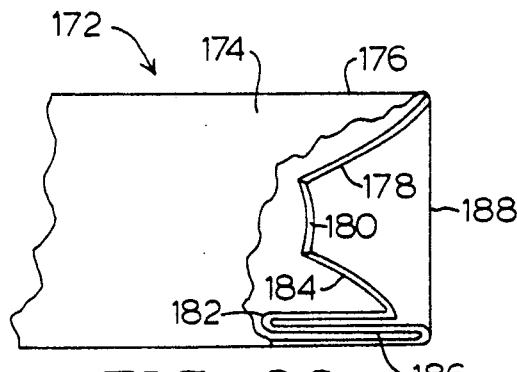
FIG. 20 is a side view, in partial cross-section, of a condom according to another embodiment of the invention.

FIG. 20 shows a partially broken away side elevation view of a condom 172 according to the present invention, such as may be produced with an extrusion blown seamless tubular body 174 forming the main sheath portion of the condom, the distal end (not shown) being sealed by heat sealing or any other suitable manner to provide a closed distal end. In this specific condom configuration, the provision of folding, as hereinafter described, avoids the need for heat sealing of the proximal opening of the condom. The proximal end 176 of this condom is formed with a membrane dam 178 having a central opening 180 therein, by folding the proximal end of tubing 174 to provide reentrant folds which are concentric with respect to one another, as shown. Thus, the distal end of the extrusion blown tube is folded back to form a first reentrant fold 182, followed by forming a second reentrant fold 184 comprising the membrane dam portion 178 and tube opening 180. There is thereby provided a three-layer structure 186 adjacent the proximal main side wall portion of the tube 174. The double reentrantly-folded tube then is heat-sealed along the proximal wall portion comprising the three-layer structure, and along the mouth of proximal end opening 188, to form a heat-sealed structure comprising an integral membrane dam configuration.

It will be recognized that the tubular stock utilized in forming the condom by reentrant folding may be reentrantly folded more than twice, or alternatively only once. The double reentrant fold configuration shown, however, provides a proximal membrane dam structure for the condom which is readily formed and provides a proximal structure which is resistant to leakage of seminal fluid.

Figure 21:
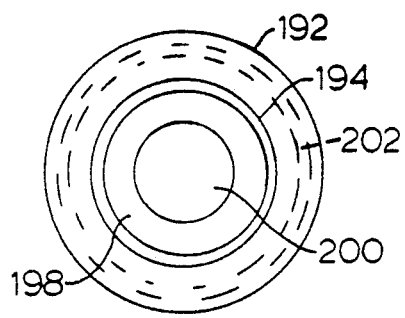
FIG. 21 is a front elevation view of a condom and applicator assembly according to one embodiment of the present invention.
Figure 22:
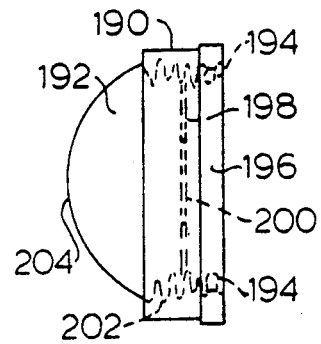
FIG. 22 is a side elevation view of the FIG. 21 condom and applicator assembly.

FIG. 21 is a rear elevation view, and FIG. 22 a side elevation view, of a condom and applicator assembly, which may advantageously be employed with thermoplastic elastomeric condoms according to the present invention, to avoid stretching of an elastic rim or ring of the condom during storage. The applicator 190 is of cylindrical shape, and may be formed of a rigid plastic, cardboard, or other suitable material of construction. The condom 192 is formed with a proximal retaining ring 194 in spaced-relationship to the rear opening of the condom, so that a length of the main sheath portion extends proximally from the retention ring 194 to the rearmost opening of the condom, as a "skirt" of the condom.

This skirt 196 is stretched and folded over the applicator 190 as shown in FIG. 22, with the retention ring 194 thus being interiorly disposed in the cylindrical applicator and maintained in an unstretched position. The condom forwardly of the retaining 194 comprises a membrane dam 198 having a central opening 200. The membrane dam thus is reposed in the interior of the applicator ring and likewise is maintained in an unstretched, relaxed condition. Distally of the membrane dam 198 is the main portion of the main sheath, which is collapsed forming a series of folds 202 which likewise are retained interiorly in the applicator.

In use, the condom 192 is applied by inserting the penis into the applicator, so that the distal end of the penis is in contact with the distal end 204 of condom 192, the penis likewise extending through the opening 200 in the membrane dam 198. The applicator ring then is drawn rearwardly towards the body of the wearer, over the length of the penis toward its base, and then the skirt of the condom is removed from the applicator, following which the applicator is passed outwardly over the penis and removed at its distal end, for subsequent disposal.

By this construction, the condom and applicator assembly of FIGS. 21-22 maintains the condom in an unstressed condition, so that no deformation of the elastic ring 194 or membrane dam 198 results.

Figure 23:
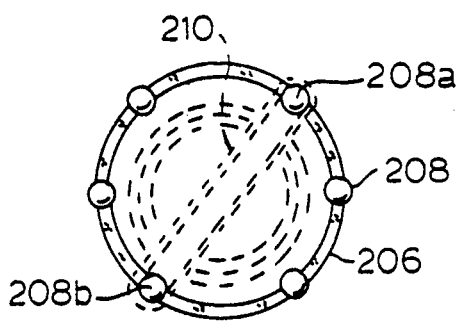
FIG. 23 is a top plan view of another applicator ring for manually applying a condom to the penis of a wearer.
Figure 24:
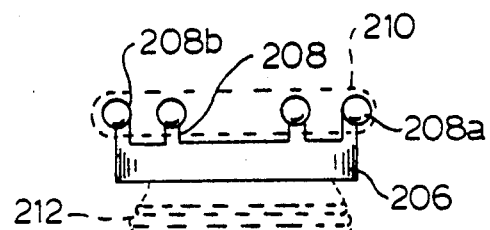
FIG. 24 is a side elevation view of the applicator ring of FIG. 23.

FIG. 23 is a top plan view, and FIG. 24 a side elevation view, of a condom applicator according to another embodiment, wherein the applicator comprises a main cylindrical portion 206 having on its upper end a series of circumferentially spaced-apart, upwardly extending prongs 208. The prongs may, as shown, feature enlarged spherical heads, or otherwise be appropriately shaped to accommodate reposing the condom thereon, without damage to or tearing of the condom.

A condom 210 is shown in dotted line representation in FIGS. 23 and 24, as being reposed at its proximal open end on a diametrally opposed pair of prongs 208a and 208b. The open proximal end of the condom thus is folded back on itself to overlay diametrally opposite prongs, to thereby retain the condom on the applicator, but without significant deformation thereof. The remaining length of the main sheath portion of the condom may be folded or gathered in any suitable fashion, such as the pleated folding 212 shown in FIG. 24.

The condom in this fashion may be packaged and stored for prolonged periods without undue stretching of the condom.

At the time of use, the condom and applicator assembly may be removed from a package (not shown) and the proximal open end of the condom is stretched onto the remaining prongs, to provide an opening of suitable dimension for insertion of the penis into the condom. Again, as in the previously described embodiment of FIGS. 21-22, the applicator 206 is rearwardly translated to the base of the penis, where the proximal extremity of the condom is removed from the prongs 208. The applicator then is drawn distally over the now-sheathed penis, and the applicator may subsequently be discarded or reused, as appropriate.

Figure 25:
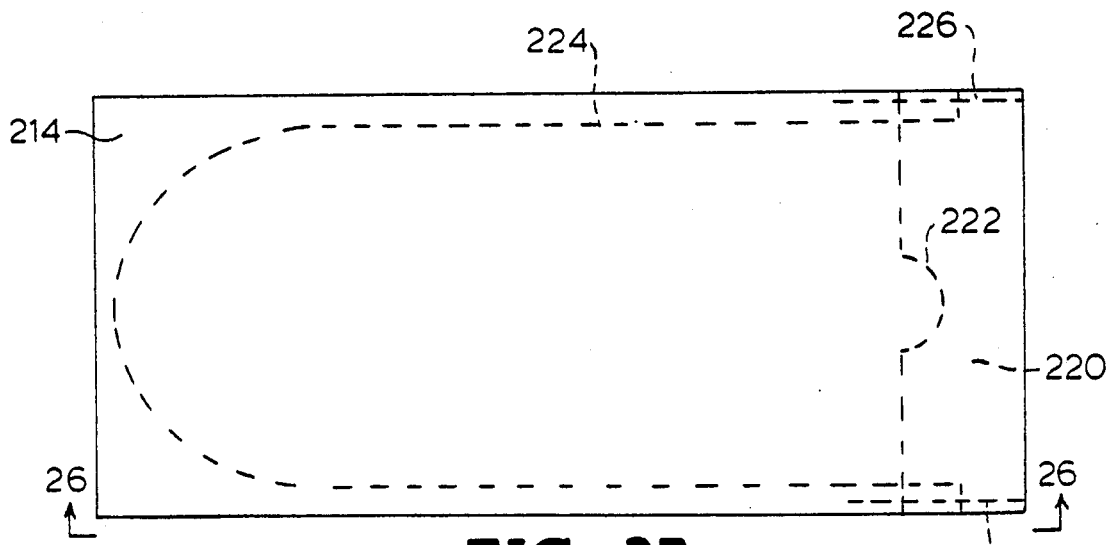
FIG. 25 is a top plan view of a folded sheet, for making a condom according to another embodiment of the invention.
Figure 26:
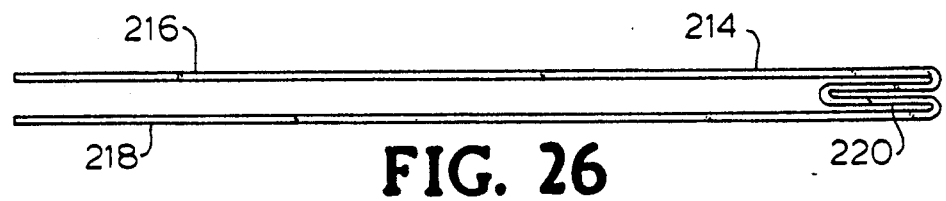
FIG. 26 is an edge elevation view of the folded sheet of FIG. 25, taken along line 26—26 thereof.

FIG. 25 is a top plan view of a folded sheet 214 such as may be usefully employed to form a condom from a suitable sheet material, such as a thermoplastic elastomer material. A corresponding edge view of the folded sheet as shown in FIG. 26, taken along line 26—26 of FIG. 25. As shown, the folded sheet comprises overlapping panel segments 216 and 218, which are co-extensively positioned with respect to one another, and a reentrant fold 220 at one extremity of the folded sheet.

A central opening 222 is provided in the reentrant fold, and may be formed initially, prior to folding of the sheet, or it may be formed in the reentrant fold material at any subsequent time during manufacture of the condom.

The central opening 222 in the reentrant fold 220 is centrally positioned in the reentrant fold material and may be configured such that the opening defines a semicircular profile when the reentrant fold is reposed in a flat configuration as shown in the top plan view of FIG. 4.

Figure 27:
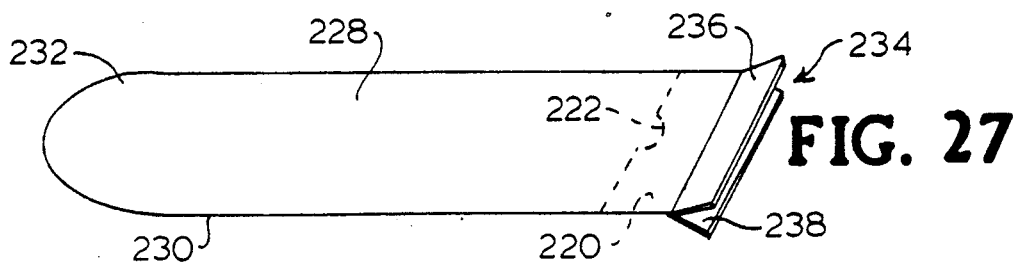
FIG. 27 is a perspective view of a condom formed from the folded sheet shown in FIGS. 25 and 26.

Subsequent to overlapping and reentrantly folding the sheet 214, the folded sheet is heat-sealed and severed along dotted line 224, and then heat-sealed and cut along marginal lines 226. The resulting product is the condom article shown in FIG. 27, comprising a main sheath portion 228 which is perimetrally sealed along its edge 230, having a closed distal end 232 and an open proximal end 234 whose proximal extremity is bounded by respective flaps 236 and 238 which provide extended surface elements for manual gripping to apply the condom to the penis of a wearer.

The reentrant fold 220 in the final configuration provides a membrane dam surrounding a central opening 222 through which the penis is inserted when the condom is applied to the body of a wearer, the membrane dam providing the function of assisting the retention of the condom on the wearer's penis, as well as to prevent fluid flow into or out of the interior volume of the condom.

Figure 28:
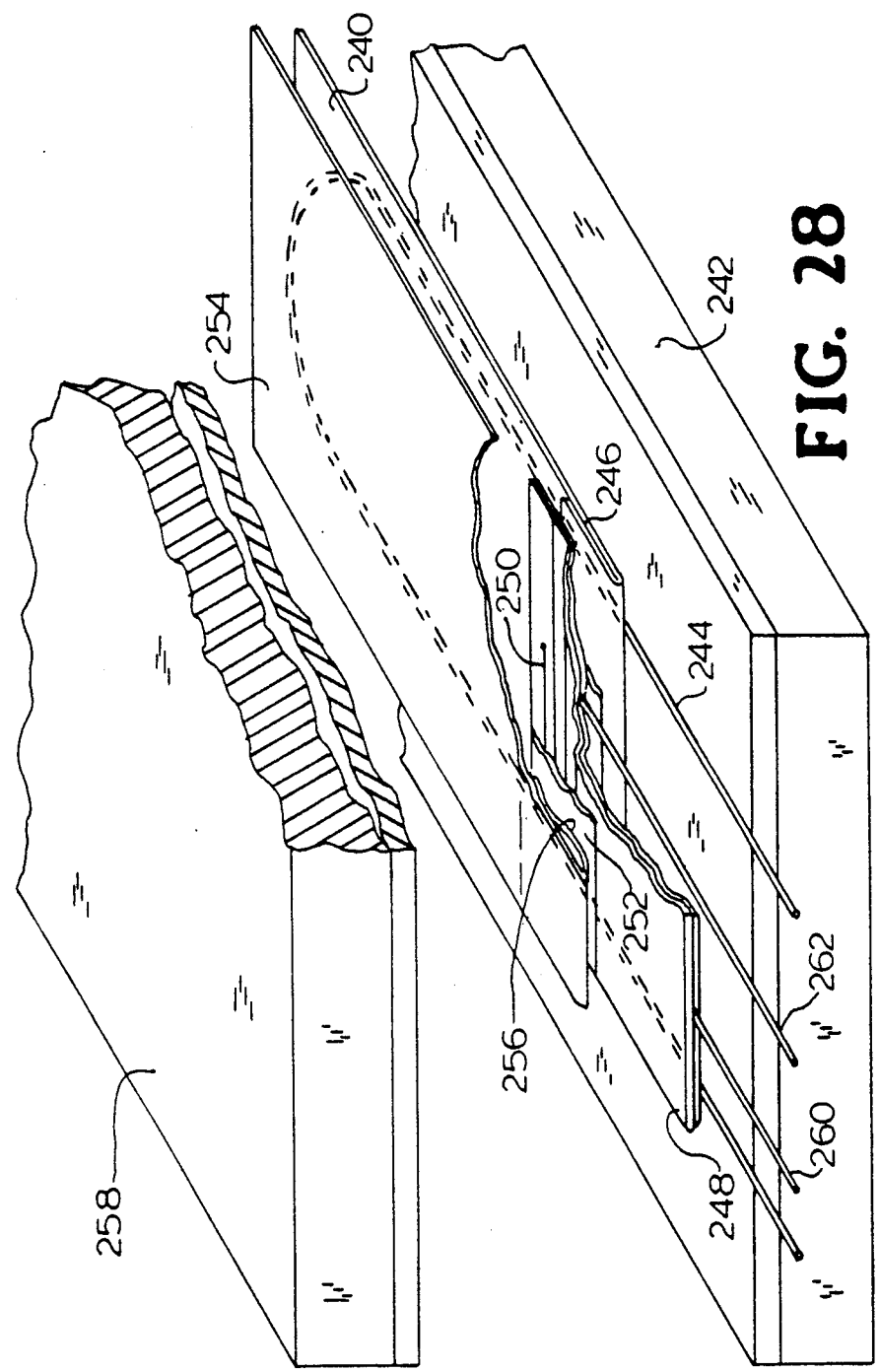
FIG. 28 is a perspective, partially broken away view of an apparatus for forming a heat-sealed condom according to the present invention.

FIG. 28 is a partially broken-away, perspective view of a manufacturing apparatus for forming a heat-sealed condom.

Referring to this drawing, a film 240 of a thermoplastic elastomer material is placed on a platen 242 over a U-shaped heat-sealing element 244, which may suitably be an electrical resistance heating wire joined to a suitable source of electrical energy (not shown for clarity). A portion of the film at the proximal end thereof is folded back on itself as shown, to provide a hem 246 as a two-layer overlapped region of the thermoplastic sheet.

The heat-sealing unit 248 comprises 2 to 4 turns of heating element wire 250, wrapped in helix. Over this heat-sealing element 248, a film tube 252, which for example may have a length (measured in the longitudinal axis of the condom being formed) of about 1 inch, and a flat width of from about 0.25 to about 0.5 times the width of the heat-sealing element 248, is stretched over the heat-sealing element 248 so that it covers the heating element wires 250. A second sheet of film material 254, folded back on itself at its proximal end to form hem 256, then is superposed on the first sheet 240, to mate co-extensively therewith.

A second platen 258 then is brought down on the superposed sheet array, and then electrical energy is sequentially or concurrently applied to the heat-sealing element 244, and the helically wound leads 260 and 262 of the heat-sealing element 248, to heat-seal the sheets to one another along a U-shaped profile defined by the U-shaped heat sealing element 244, and to heat seal the stretched film tube 252 to the interior surface of the hems 246 and 256. The resulting article then is removed form the forming apparatus, and trimmed.

There is resultingly formed a condom comprising the stretched film tube 252 bonded to the two hems, to function as an elastic garter to contract the opening uniformly around its circumference at the proximal end of the condom.

It will be appreciated that in lieu of the specific film tube 252 employed to form the elastic garter in the condom formed by the apparatus in FIG. 28, it may be advantageous to use a suitable elastic ribbon which is circumferentially wrapped around the heating element 248 and held in position by spot welding or otherwise securing the respective overlapping ends thereof to one another.

Figure 29:
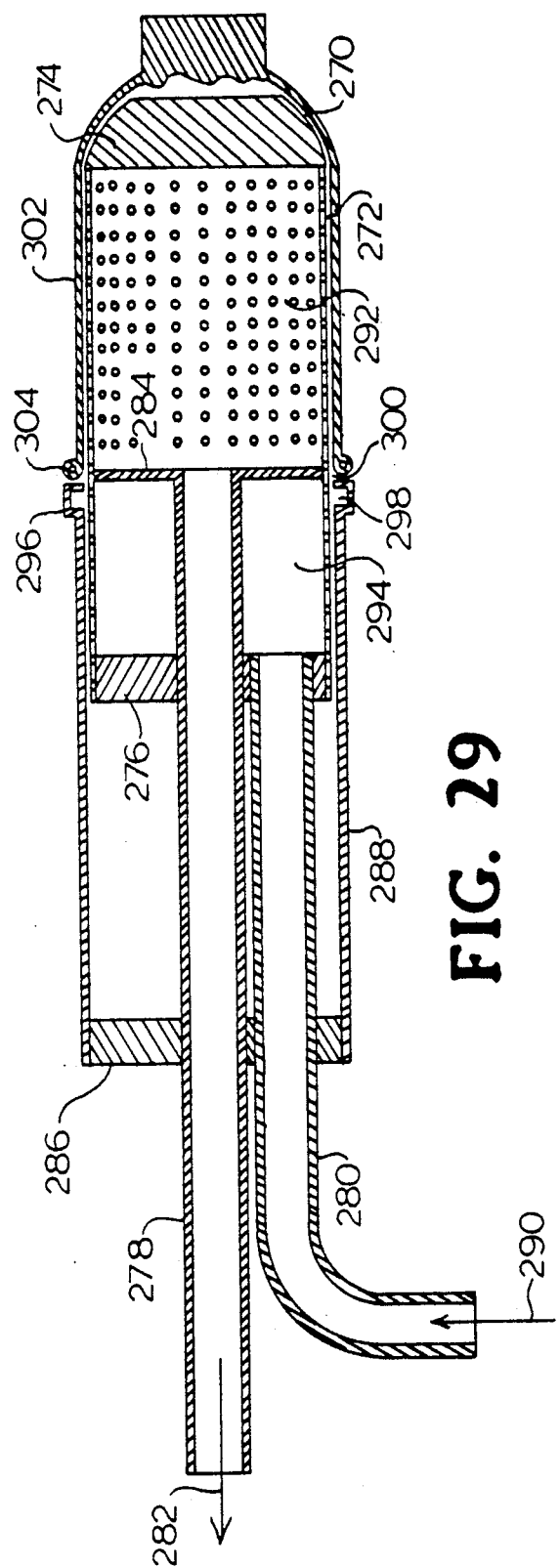
FIG. 29 is a condom rolling device for forming rolled condoms.

FIG. 29 is a cross-sectional view of a condom rolling apparatus, such as may be usefully employed to roll condoms for packaging and/or storage prior to use.

The apparatus comprises a stationary cylinder 270 comprising a main cylindrical surface 272 which is perforated over substantially its entire areal extent, and bounded by a distal bulkhead 274 and a proximal wall 276. The proximal wall 276 has a central opening to accommodate axial sliding movement therein of the evacuation conduit 278. The proximal wall 276 also is provided with a suitable opening within which is disposed the distal end of pressurizing conduit 280.

The openings in proximal wall 276 are appropriately sized to accommodate the respective conduits 278 and 280 in a leak-tight fashion. For example, the juncture between proximal wall 276 and the reciprocatable, axially slidable conduit 278 may be accommodated by a suitable O-ring or other sealing means, such as a packing ring structure. The juncture between proximal wall 276 and pressurizing conduit 280 may be leak-tightly secured by welding of the conduit to the wall at the appertaining opening.

The vacuum withdrawal conduit 278 is joined to suitable evacuation means, such as a pump or blower (not shown for clarity), so that the flow of gas being evacuated is in the direction indicated by arrow 282. The vacuum withdrawal conduit 278 is fixedly secured at its distal end to an annular-shaped baffle plate 284, the baffle plate being of sufficient size to accommodate a sealed longitudinal sliding movement of the baffle plate in the interior volume of stationary cylinder 270.

The vacuum withdrawal conduit 278 is fixedly secured to the end wall 286 of a movable outer cylinder 288 which is coaxial with and overlies the stationary inner cylinder 270. The end wall 286 of the movable outer cylinder 288 also has an opening therein to accommodate the slidable passage therethrough of pressurizing conduit 280. The pressurizing conduit 280 is connected at its proximal end to a suitable gas supply means such as for example an air compressor (not shown for clarity), to introduce gas at elevated pressure into conduit 280 in the direction indicated by arrow 290.

The annular plate 284 thus at any given point of axial translation of the movable outer cylinder divides the interior volume of the inner cylinder 270 into a distal compartment 292 which is evacuated to be at a relatively lower pressure, and a proximal chamber 294 which is pressurized by gas introduced from pressurizing conduit 280, so as to be at a relatively higher pressure level.

The distal end of the movable outer cylinder 288 features a circumferentially extending collar 296 enclosing an inner circumferentially extending volume 298 which receives gas from the pressurizing chamber 294 through openings in the perforated wall 272 of the inner cylinder, and discharges same distally of the outer cylinder through the discharge slot 300 between the distal lip of the collar and the surface of the inner cylinder 272.

In use, the outer cylinder 288 is proximally retracted, and a condom 302 is applied over the exterior surface of the inner cylinder 270. The distal chamber 292 in such cylinder then is evacuated through the gas withdrawal passage 278, so that the negative pressure gradient thereby produced retains the condom on the inner cylinder against movement.

Concurrently, gas is introduced into the pressurizing conduit 280 and the outer cylinder is translated axially forwardly, so that gas is discharged from the annular discharge slot 300 between the respective cylinders to cause the condom to roll forwardly and produced a rolled configuration 304, as the outer cylinder is axially forwardly translated to its maximum distal extent.

At the maximum distal extent of travel of the outer cylinder relative to the inner cylinder, the rolled condom is removed from the cylinder at the bulkhead wall 274 and packaged and/or stored for subsequent use.

FIG. 30 is a cross-sectional, elevation view, and FIG. 31 a top plan view, of a heat-sealing and thermoforming apparatus for making condoms.

The apparatus comprises an outer cylindrical shell 306 joined at its lower portion to end block 308, by means of straps 310, to allow loose fitting of the end block 308 to the cylindrical shell 306. The end block 308 suitably is formed with a concave contour 312 approximating the frontal contour of the condom to be formed.

In the interior volume 314 defined by the cylindrical shell 306, there is disposed a pouch 316 of extruded or heat-sealed tubular film with a heat-sealed closed distal end 318.

At the upper portion of the cylindrical shell 306 is interiorly mounted a second end block 320 having a central cylindrical passage 322 therein. Disposed in passage 322 is a compression stopper which is diametrically expandable by tightening nut 326 against washer 328.

A balloon 330, formed of a suitable material such as latex, is reposed interiorly of the tubular film pouch 316. The respective necks of the balloon 330 and the tubular film pouch 316 are compressed between the inner wall surface of cylindrical passage 322 of the end block 320, and the compression stopper 324.

The neck of the balloon 330 is cemented or otherwise affixed permanently to the compression stopper 324. A central tube 332 is interiorly disposed in the balloon 330 and acts as a mandril for the compression stopper 324. The tube 332 also provides an air inlet, being open at its lower end, for inflating the inner balloon and outer thermoplastic tubular film. The upper end of this tube is connected to a selectively controllable source of pressurized gas (not shown for clarity).

In use, the tubular film pouch 316 is pulled over the balloon 330 and the compression stopper 324. The stopper and attached pouch then are placed in the assembly as shown in FIG. 29, and the balloon and pouch are sealed by compressing the compression stopper, via tightening of the compression nut 326. The pouch 316 then is inflated, by introducing into the balloon from gas flow passage 336 of tube 332, air or other pressurizing gas, as for example air at a pressure of 1-3 psig.

The entire assembly as illustrated in FIG. 30 then is placed in an elevated temperature medium, such as boiling water or an oven at a sufficient thermoforming temperature. After sufficient exposure to the elevated temperature conditions, which may for example involve an exposure time on the order of 0.5 to 3 minutes, the assembly is quenched in a suitable quenching medium such as water at ambient temperature, or by air blast exposure to air at ambient temperature.

The forming assembly then is disassembled, and the thermoplastic condom, produced by expansion of the pouch 316 to conform to the interior shape of the cylindrical shell 306 and the interior contours of the end blocks 308 and 320, is removed from the compression stopper after it has been loosened and contracted to a suitable diametral extent allowing for removal of the finished condom. Thus, a condom is formed which has assumed the shape of the interior bounding surfaces of the thermoforming assembly, and a reduced diameter neck is retained on the condom to facilitate retention on the penis of a wearer in use.

Figure 32:
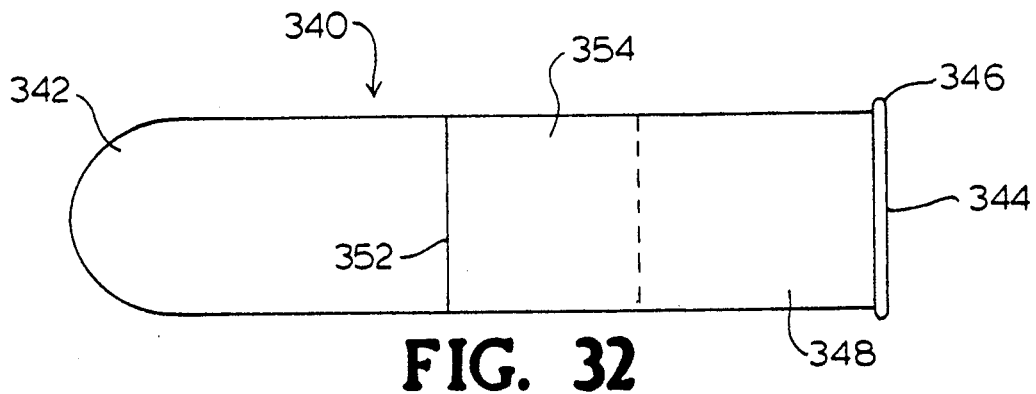
FIG. 32 is a side elevation view of a condom according to another embodiment of the invention.
Figure 33:
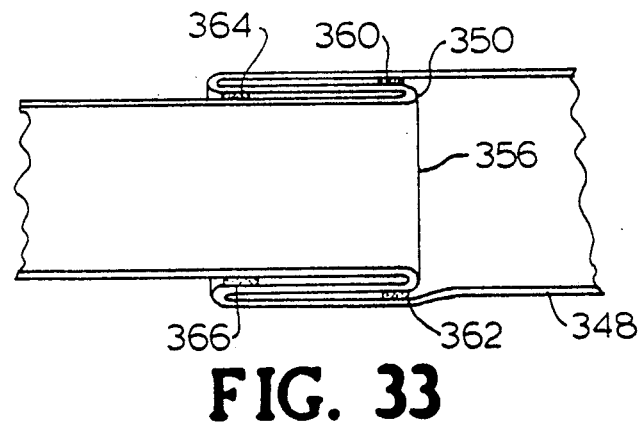
FIG. 33 is a sectional elevation view of the medial portion of the FIG. 32 condom.

FIG. 32 shows a top plan view of a condom according to another embodiment of the invention, and FIG. 33 shows a cross-section of the condom at an intermediate portion of its length between its closed distal end 342 and its open proximal end 344, which may be circumferentially bounded by an elastic retaining ring 346, or other suitable retention structure. The main sheath portion of the condom 348 is axially overlapped by the provision of a reentrant fold 350, thereby yielding a condom with a distal leading edge 352 of an axially overlapped section 354, the overlapped section interiorly terminating at a proximal edge 356 of the reentrant fold, as shown in FIG. 33.

The axially overlapped intermediate section 354 thus comprises a three-layered fold construction, and adjacent layers in the folded construction are secured to one another by the spot welds 360 and 362, securing the adjacent outer layers, and the spot welds 364 and 366, securing the adjacent inner layers of the folded construction to one another.

It will be apparent from the foregoing that the axial overlapping produced by reentrant folding of the condom in the manner described will shorten the condom to a length which is less than the initial fully extended length of the condom, by an extent which is approximately twice the axial extent of the intermediate folded section 354. If, in use, it is desired that the condom have a length which is greater than that provided with the overlapped configuration, it simply is necessary to rearwardly (proximally) extend the proximal portion of the condom relative to the distal portion thereof, to break the spot or tack welds 360, 362, 364, and 366, thereby extending the condom to its original fully extended length (prior to reentrant folding thereof).

In lieu of the tack welds, there may be provided discrete amounts of adhesive or other bonding medium, or the respective layers of the reentrant fold may be secured to one another in any other suitable manner which does not adversely affect the structural integrity of the condom when the attachments between respective layers are broken and the condom is lengthened to a fully extended condition.

It will be appreciated from the foregoing that the condom may be reentrantly folded at additional positions along its length, to provide for greater variability in the length of the condom, so that if breaking of the bonds between adjacent layers of a first reentrant fold does not produce a condom of desired length characteristics, then an additional reentrant fold may be unfolded by breakage of the attachments between adjacent layers thereof, to provide the additional length desired.

Figure 34:
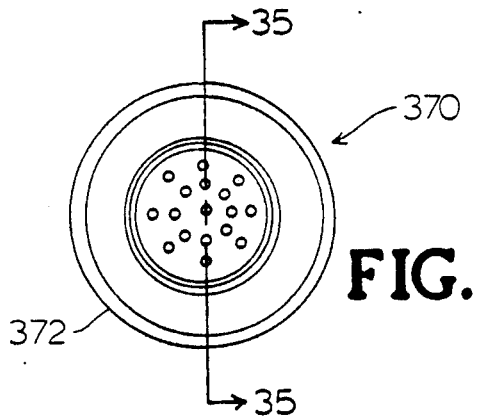
FIG. 34 is a top plan view of a thermoformer apparatus for forming condoms.
Figure 35:
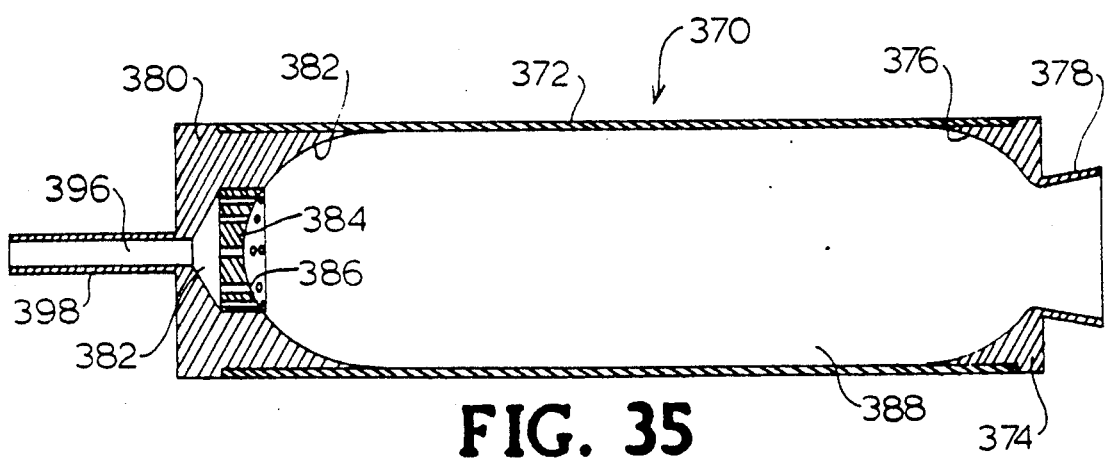
FIG. 35 is a side elevation view of a section of the FIG. 34 thermoformer apparatus, taken along line 35—35 thereof.

FIG. 35 is a top plan view, and FIG. 35 a corresponding side elevation view in cross-section, taken along line 35—35 of FIG. 34, showing a thermoformer apparatus for forming condoms. The thermoformer device 370 comprises a cylindrical shell 372, joined at one end to an end block 374 having a generally concave interior surface 376 extending convergingly toward an outwardly flaring mouth 378 of the block.

At its opposite end, the cylindrical shell 372 is joined to a second end block 380 providing a concave surface profile approximating the contour of a condom to be formed by the device. In the frontal cavity 382 of this end block is disposed a perforate insert 384, comprising a series of axially extending, laterally spaced-apart gas flow passages 386, by means of which the main interior volume 388 in the cylindrical casing 372 communicates with the cavity 382 and the interior gas flow passage 396 of gas removal conduit 398.

The gas removal conduit 398 in use is attached to a suitable gas evacuation means, as for example a blower or vacuum pump (not shown for clarity). A tubular film article, sealed at one end thereof, and serving as a preform or precursor article for the condom to be manufactured, then is attached at its open end to the exterior surface of the mouth 378 of end block 374. In other words, the tubular preform features an open distal end which is stretched over the mouth of end block 374, so that the condom preform is exteriorly extended from the end block mouth.

The gas evacuation means then is actuated to withdraw air from the interior cavity 388 of the cylindrical housing 372, through the gas flow passages 386 and cavity 382, for discharge from the thermoformer apparatus in gas withdrawal conduit 398. Such evacuation draws the condom preform in inverted fashion into the interior cavity 388 of the thermoformer, where the pressure differential forces the condom preform to assume the shape of such interior cavity.

A stopper (not shown) of a size accommodating leak-tight fitting to the mouth 378 of end block 374 then is placed in the mouth, while negative pressure is maintained on the interior cavity to retain the condom preform in expanded condition, assuming the shape of the interior cavity of the thermoformer.

The thermoformer then is subjected to elevated temperature (by means not shown), such as for example a heating tape or electrical resistance element helically wrapped onto cylindrical casing 372, to cause the casing and end blocks to reach a suitable thermoforming temperature, as for example on the order of about 250° F., at which the expanded condom will be thermally permanently conformed to the contours of the cavity 388. Subsequent to achievement of the thermoforming temperature, the thermoforming assembly is cooled to ambient temperature, and the negative pressure differential imposed on the thermoplastic film discontinued.

The now formed condom may subsequently be removed from the thermoforming apparatus by flowing a gas at suitable elevated pressure through conduit 396, cavity 382 and gas flow passages 386 into the cavity 388, whereby the condom is forced outwardly from the thermoformer after the stopper has been removed from mouth 378.

While the invention has been described with reference to specific embodiments and features, it will be appreciated that numerous modifications, variations, and embodiments of the invention are possible, and all such apparent variations, modifications, and embodiments are therefore to be regarded as being within the spirit and scope of the invention.

What is claimed is:

1. A condom, comprising:
    a generally tubular main sheath portion (i) of elongate form, (ii) defined by an enclosing wall formed of a thermoplastic elastic material, (iii) enclosing an interior volume of the condom, and (iv) closed at a distal end thereof and open at a proximal end thereof;
    a proximal segment comprising a continuous reentrant fold of the enclosing wall (i) longitudinally extending into and terminating in the interior volume of the condom, (ii) having a central opening therein of smaller size than the proximal end opening, and (iii) marginally sealed to the main sheath portion at diametrally opposed side margins of the main sheath portion.

2. A condom according to claim 1, wherein the marginal seals are heat seals.

3. A condom according to claim 1, wherein the main sheath portion is formed of a thermoplastic elastic polyurethane material.

4. A condom according to claim 1, comprising diametrally opposed heat seals extending longitudinally along the main sheath portion and converging at said distal end thereof, with the reentrant fold being marginally sealed by said diametrally opposed heat seals.

5. A condom according to claim 1, with proximal end flanges at the proximal open end, and with the reentrant fold being continuous with said flanges, with heat seals along longitudinal side edges of the condom extending from the distal end to the proximal end flanges thereof flanges.

6. A condom according to claim 1, wherein said thermoplastic elastomeric material is selected from the group consisting of: polyurethanes; polyether block amides; styrene-rubber-styrene block copolymers; polyesters; olefinic homopolymers and copolymers; and copolymers, composites, and alloys thereof.

7. A condom according to claim 1, wherein the main sheath portion and sealing element are formed of polyurethane material having: a specific gravity of from about 1.00 to 1.25; a Shore A hardness of from about 80 to about 100; a break tensile strength of from about 4,500 to about 6,000 psi; a tensile stress at 50% elongation of from about 400 to about 2400 psi; an ultimate elongation of from about 350% to about 600%; a flexural modulus of from about 4,000 to about 37,000 psi; and a tear strength of from about 500 to about 1,000 pli.

8. A condom according to claim 1, wherein the main sheath portion has a thickness of from about 0.05 to about 0.25 millimeter.

9. A condom according to claim 1, wherein the main sheath portion has a thickness of from about 0.05 millimeter to about 0.1 millimeter.

10. A condom according to claim 1, wherein the main sheath portion has a diameter on the order of about 2 inches, and the central opening in the reentrant fold has a diameter on the order of 0.5 inch.

11. A method of making a condom, comprising the steps of:
(a) providing a sheet of a thermoplastic elastic film;
(b) laterally folding said sheet along a lateral fold line to provide lapped main panel portions of the folded sheet;
(c) forming an opening in the laterally folded sheet at an intermediate part of the lateral fold line;
(d) longitudinally inserting a portion of the sheet comprising the fold line reentrantly into the folded sheet to position the fold line between the folded sheet main panel portions and at a leading edge of the inserted reentrant portion; and
(e) heat sealing the folded sheet along lateral peripheral margins thereof, from the inserted reentrant portion forwardly to a distal portion thereof, to sealingly enclose an interior volume of the folded sheet, with the reentrant portion heat sealed at lateral peripheral margins thereof to the lateral peripheral margins of the main panel portions of the folded sheet.

12. A method according to claim 11, wherein said thermoplastic elastic material is selected from the group consisting of: polyurethanes; polyether block amides; styrenerubber-styrene block copolymers; polyesters; olefinic homopolymers and copolymers; and copolymers, composites, and alloys thereof.

13. A method according to claim 11, wherein said sheet is formed of a polyester-based polyurethane.

14. A condom article, comprising;
a generally tubular main sheath portion, closed at a distal end thereof and opened at a proximal end thereof, formed by elongate superposed panels (i) continuously perimetrally heat-sealed to one another along side and distal margins thereof to form an interior volume of the condom bounded by the panels, and (ii) formed of a flexible thermoplastic elastomeric material; and
a proximal segment comprising a continuous reentrant fold portion of the panels (i) longitudinally extending into and terminating in the interior volume of the condom, (ii) having a central opening therein of smaller size than the proximal end opening, and (iii) marginally sealed to the main sheath portion at diametrally opposed side margins of the main sheath portion.

* * * * *

UNITED STATES PATENT AND TRADEMARK OFFICE
CERTIFICATE OF CORRECTION

PATENT NO. : 5,036,863

DATED : August 6, 1991

INVENTOR(S) : Robert G. Wheeler

It is certified that error appears in the above-identified patent and that said Letters Patent is hereby corrected as shown below:

Column 10, line 21, change "blockamides" to --block amides--.

Column 21, line 34, after "annular" insert --baffle--.

Signed and Sealed this

Second Day of March, 1993

Attest:

STEPHEN G. KUNIN

*Attesting Officer*     *Acting Commissioner of Patents and Trademarks*

UNITED STATES PATENT AND TRADEMARK OFFICE
CERTIFICATE OF CORRECTION

PATENT NO. : 5,036,863
DATED : August 6, 1991
INVENTOR(S) : ROBERT G. WHEELER

It is certified that error appears in the above-identified patent and that said Letters Patent is hereby corrected as shown below:

In Column 1, after the title, insert

-- <u>GOVERNMENT LICENSE RIGHTS</u>

The invention claimed herein was made under one or more of the following contracts: U.S. Agency for International Development Contract Nos. DPE-3041-A-00-0043 and DPE-0537-A-00-4047, and National Institutes of Health Contract No. N01-HD-2-3143, and the U.S. government has certain rights therein. --

Signed and Sealed this

Twenty-second Day of November, 1994

Attest:

BRUCE LEHMAN

*Attesting Officer*    *Commissioner of Patents and Trademarks*